(12) United States Patent
De Strooper et al.

(10) Patent No.: US 11,346,848 B2
(45) Date of Patent: May 31, 2022

(54) Γ-SECRETASE STABILIZING COMPOUND SCREENING ASSAY

(71) Applicants: VIB VZW, Ghent (BE); KATHOLIEKE UNIVERSITEIT LEUVEN, K.U.LEUVEN R&D, Leuven (BE)

(72) Inventors: Bart De Strooper, Leuven (BE); Lucia Chávez Gutiérrez, Herent (BE); Maria Szaruga, Leuven (BE)

(73) Assignees: VIB VZW, Ghent (BE); Katholieke Universiteit Leuven, KU Leuven R&D, Leuven (BE)

( * ) Notice: Subject to any disclaimer, the term of this patent is extended or adjusted under 35 U.S.C. 154(b) by 0 days.

(21) Appl. No.: 16/477,391

(22) PCT Filed: Jan. 10, 2018

(86) PCT No.: PCT/EP2018/050537
§ 371 (c)(1),
(2) Date: Jul. 11, 2019

(87) PCT Pub. No.: WO2018/130555
PCT Pub. Date: Jul. 19, 2018

(65) Prior Publication Data
US 2019/0339292 A1    Nov. 7, 2019

(30) Foreign Application Priority Data

Jan. 12, 2017  (EP) ..................... 17151239
Feb. 20, 2017  (EP) ..................... 17156869

(51) Int. Cl.
*G01N 33/68* (2006.01)
*C12Q 1/37* (2006.01)

(52) U.S. Cl.
CPC .......... *G01N 33/6896* (2013.01); *C12Q 1/37* (2013.01); *G01N 2333/4709* (2013.01); *G01N 2500/02* (2013.01); *G01N 2800/2821* (2013.01)

(58) Field of Classification Search
CPC ....... G01N 33/6896; G01N 2333/4709; G01N 2500/02; G01N 2800/2821; C12Q 1/37
See application file for complete search history.

(56) References Cited

U.S. PATENT DOCUMENTS

2010/0120874 A1  5/2010  Baumann et al.
2012/0289558 A1  11/2012  Kounnas et al.

OTHER PUBLICATIONS

Matsumura et al., J Biol Chem, vol. 289, No. 8, pp. 5109-5121, Feb. 21, 2014 (Year: 2014).*
Macias et al. J Neurosci Methods, 223:114-122 (Year: 2014).*
Jung et al. Cholestenoic acid, an endogenous cholesterol metabolite, is a potent -secretase modulator. Molecular Neurodegeneration, Biomed Central Ltd, LO, vol. 10, No. I, Jul. 14, 2015 (Jul. 14, 2015), p. 29, XP021227996, ISSN: 1750-1326, DOI:10.1186/SI3024-015-0021-Z the whole document, p. 10-11 bridging paragraph, figure 1.
Mitani et al. Pharmacological Characterization of the Novel [gamma]-Secretase Modulator AS2715348, a Potential Therapy for Alzheimers Disease, in Rodents and Nonhuman Primates. Neuropharmacology., vol. 79, Apr. 1, 2014 (Apr. 1, 2014), pp. 412-419, XP055459350, ISSN: 0028-3908, DOI: 10.1016/j.neuropharm.2013.12.013 the whole document, sections 2.4.1, 2.4.2, 3.1, figure 2.
PCT International Search Report and Written Opinion, Application No. PCT/EP2018/050537, dated Jun. 7, 2018, 19 pages.
Quintero-Monzon et al. Dissociation between the Processivity and Total Activity of [gamma]-Secretase: Implications for the Mechanism of Alzheimers Disease-Causing Presenilin Mutations. Biochemistry, vol. 50, No. 42, Oct. 25, 2011 (Oct. 25, 2011), pp. 9023-9035, XP055459357, us ISSN: 0006-2960, DOI: 10.1021/bi2007146 the whole document, abstract.
Szaruga et al., Alzheimers-Causing Mutations Shift A[beta] Length by Destabilizing [gamma]-Secretase-A[beta]n Interactions, Cell, vol. 170, No. 3, Jul. 1, 2017 (Jul. 1, 2017), pp. 443-456.el4, XP055459359, ISSN: 0092-8674, DOI:10.1016/j.cell.2017.07.004, the whole document.

* cited by examiner

*Primary Examiner* — Kimberly Ballard
*Assistant Examiner* — Stacey N MacFarlane
(74) *Attorney, Agent, or Firm* — Patent Law Works, LLP

(57) ABSTRACT

The present invention relates to the field of neurodegenerative diseases. More specifically, the present invention relates to a screening assay to produce compounds stabilizing the gamma-secretase enzyme substrate complex, thereby increasing gamma-secretase processivity while attenuating the release of longer Aβ peptides. More specifically, gamma-secretase stabilizing compounds increase thermostability of the enzyme/substrate complexes acting in the sequential γ-secretase processing of APP, to result in reduced amyloidogenic Aβ production, thereby preventing Alzheimer disease.

11 Claims, 17 Drawing Sheets
(16 of 17 Drawing Sheet(s) Filed in Color)
Specification includes a Sequence Listing.

A

C

D

SEQUENCE LISTING

<160> NUMBER OF SEQ ID NOS: 5

<210> SEQ ID NO 1
<211> LENGTH: 695
<212> TYPE: PRT
<213> ORGANISM: Homo sapiens

<400> SEQUENCE: 1

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365
```

-continued

Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
            405                 410                 415

Asn Met Leu Lys Lys Tyr Val Arg Ala Glu Gln Lys Asp Arg Gln His
        420                 425                 430

Thr Leu Lys His Phe Glu His Val Arg Met Val Asp Pro Lys Lys Ala
    435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
        500                 505                 510

Tyr Gly Asn Asp Ala Leu Met Pro Ser Leu Thr Glu Thr Lys Thr Thr
    515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
            565                 570                 575

Thr Arg Pro Gly Ser Gly Leu Thr Asn Ile Lys Thr Glu Glu Ile Ser
        580                 585                 590

Glu Val Lys Met Asp Ala Glu Phe Arg His Asp Ser Gly Tyr Glu Val
    595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
        660                 665                 670

His Leu Ser Lys Met Gln Gln Asn Gly Tyr Glu Asn Pro Thr Tyr Lys
    675                 680                 685

Phe Phe Glu Gln Met Gln Asn
690                 695

<210> SEQ ID NO 2
<211> LENGTH: 99
<212> TYPE: PRT
<213> ORGANISM: Homo sapiens

<400> SEQUENCE: 2

Asp Ala Glu Phe Arg His Asp Ser Gly Tyr Glu Val His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Gln Tyr Thr Ser Ile His His Gly Val
        50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn

<210> SEQ ID NO 3
<211> LENGTH: 46
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr Val Ile Val
            35                  40                  45

<210> SEQ ID NO 4
<211> LENGTH: 45
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr Val Ile
            35                  40                  45

<210> SEQ ID NO 5
<211> LENGTH: 32
<212> TYPE: PRT
<213> ORGANISM: Homo sapiens

<400> SEQUENCE: 5

Leu Pro Ser Gln Leu His Leu Met Tyr Val Ala Ala Ala Ala Phe Val
1               5                   10                  15

Leu Leu Phe Phe Val Gly Cys Gly Val Leu Leu Ser Arg Lys Arg Arg
                20                  25                  30

Γ-SECRETASE STABILIZING COMPOUND SCREENING ASSAY

FIELD OF THE INVENTION

The present invention relates to the field of neurodegenerative diseases. More specifically, the present invention relates to a screening assay to produce compounds stabilizing the gamma-secretase enzyme substrate complex, thereby increasing gamma-secretase processivity while attenuating the release of longer Aβ peptides. More specifically, gamma-secretase stabilizing compounds increase thermostability of the enzyme/substrate complexes acting in the sequential γ-secretase processing of APP, to result in reduced amyloidogenic Aβ production, thereby preventing Alzheimer disease.

BACKGROUND

Finding a therapy for Alzheimer's disease (AD) is one of the biggest challenges of current medicine. Genetics has shown that single mutations in functionally related genes cause early onset familial AD (FAD) in an autosomal dominant manner providing a unique model to investigate AD pathogenic mechanisms. More than 200 mutations in Presenilin 1 or 2 (PSEN1/2) (*Enzyme*) (Sherrington et al., 1995) and about 20 in the Amyloid Precursor Protein (APP) (*Substrate*) (Goate et al., 1991) strongly support the relevance of Aβ (*Products*) in AD pathogenesis. PSEN1/2 are the catalytic subunits of distinct γ-secretase intramembrane protease complexes (De Strooper et al., 1998; Wolfe et al., 1999), which additionally contain Nicastrin (NCT), Presenilin-enhancer 2 (PEN2) and the Anterior pharynx defective 1 (APH1) as essential components (De Strooper and Chávez Gutiérrez, 2015). Alzheimer's disease (AD) linked mutations in Presenilins (PSEN) and the Amyloid Precursor Protein (APP) lead to production of longer amyloidogenic Aβ peptides. Several studies point to long Aβ peptides ($\geq A\beta_{42/43}$) as key players that initiate aggregation of toxic Aβ-derived species, which ultimately lead to neurodegeneration in AD (Benilova et al., 2012; Haass and Selkoe, 2007). Although it is generally known that longer Aβ peptides ($>A\beta_{42/43}$) lead to neurodegeneration, the theoretical basis for gamma-secretase substrate recognition and cleavage specificity of Aβ peptides to a different length is not known.

γ-Secretases generate Aβ peptides of different length from APP, and AD causative PSEN mutations consistently decrease γ-secretase processivity (number of cuts per substrate molecule) thereby shifting Aβ profiles towards longer and therefore more amyloidogenic peptides (Chávez-Gutiérrez et al., 2012; Fernandez et al., 2014). Although highly relevant, mechanistic understanding of γ-secretase function is very limited, e.g. we do not know how γ-secretase recognizes substrates, what drives the sequential cleavage of APP or how clinical mutations in PSEN lead to the release of longer Aβ peptides. As a result, the lack of fundamental knowledge has set controversial discussion about the pathogenic role of PSEN (Veugelen et al., 2016) and has made γ-secretase an extremely challenging target for AD therapeutics (for discussion see De Strooper and Chavez, 2015).

The recent γ-secretase structures (Bai et al., 2015a, 2015b) (FIG. 8A) depict PSEN with a loosely organized, likely metastable fold, that co-exist in several conformations. These findings are in line with previous low resolution structural analyses (Elad et al., 2014; Li et al., 2014), as well as, with FRET-based studies presenting the PSEN/γ-secretase complex as a very dynamic entity (Lleo et al., 2004; Uemura et al., 2009, 2010; Wahlster et al., 2013). Interestingly, elegant studies on rhomboid intramembrane proteases depict them as intrinsically metastable proteolytic systems (Baker and Urban, 2012). If PSEN structure, as rhomboids, relied on a network of weak interactions throughout the molecule, one could hypothesize that scattered FAD-linked PSEN mutations further affect its metastable fold and impact protease function. γ-Secretase exerts a complex proteolytic activity (Takami et al., 2009). An initial ε-endopeptidase cleavage releases the soluble intracellular domain (AICD) and generates a membrane-anchored fragment (either $A\beta_{49}$ or $A\beta_{48}$) that is successively cut by carboxypeptidase-like γ-cleavages generating shorter $A\beta_n$ peptides (FIG. 1A) until Aβ release stops the process. Accordingly, the sequential processing of APP by γ-secretase involves the formation of distinct enzyme-substrate (E-S) complexes, which each contain shortened de novo $A\beta_n$ substrates. Development of γ-secretase modulators (GSM) retaining ε-endopeptidase cleavage efficacy and stimulating the carboxypeptidase cleavage has been suggested as a more promising therapeutic target (Bai et al. 2015).

It would be advantageous to elucidate the dynamics of the γ-secretase in complex with APP or intermediate cleaved $A\beta_n$ products thereof, to allow insights into alternative mechanisms of action of γ-secretase modulators (GSMs) as potential therapeutics for AD. It should be evaluated whether the strength or stability of the productive Enzyme-Substrate (E-S) interactions between γ-secretase and APP/$A\beta_n$, respectively, is correlated to the length of the Aβ substrates. It would also be interesting to explore whether pathogenic PSEN mutations can be correlated to a destabilization of the E-S interaction with APP- and $A\beta_n$-substrates, leading to enhanced dissociation/release of aggregation-prone, longer Aβ peptides.

SUMMARY OF THE INVENTION

The present invention relates to a method for producing gamma-secretase stabilizing compounds via screening of compounds in gamma-secretase complex-destabilizing conditions, such as increased temperature conditions, or in the presence of denaturing agents such as detergent, to identify those compounds that are capable in stabilizing the consecutive enzyme/substrate complexes that characterize the sequential γ-secretase processing of APP. Said γ-secretase/substrate stabilizing compounds (GSSCs) result in reduced annyloidogenic Aβ peptide production, thereby preventing Alzheimer disease.

In one aspect, the invention relates to a method for producing a gamma-secretase stabilizing compound comprising the steps of, a) providing a system comprising a gamma-secretase complex, and a (poly)peptide SEQ ID NO:1 [APP] or a homologue with 95% amino acid identity thereof, or any fragment thereof, and b) administering a test compound to said system, and incubating said system in gamma-secretase complex-destabilizing conditions, and c) quantification of the Aβ peptides produced in said system, wherein, under the same test conditions as compared to the same system without the test compound, an increase in the ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ peptides identifies said test compound as a gamma-secretase stabilizing compound.

In a specific embodiment, said gamma-secretase complex-destabilizing conditions are induced by incubating said system at one or more temperature(s) in the range of about 35° C. to about 65° C., or more particular, in the range of about 37° C. to about 55° C. In another embodiment, said gamma-secretase complex-destabilizing conditions are induced by addition or presence of a denaturing agent or detergent in the system for its incubation upon addition of the test compound in step b).

In one embodiment, said provided system is an in vitro system. In a particular embodiment, said in vitro system comprises a detergent resistant membrane preparation. Or alternatively, said provided system is a cell-based or in vivo system.

In another embodiment, said method is characterized in that the provided system comprises a gamma-secretase complex and a (poly)peptide SEQ ID NO:1 [APP] or a homologue with 95% amino acid identity thereof, or any fragment of SEQ ID NO:1 or of the 95% identity homologue of SEQ ID NO:1, wherein said fragment comprises at least 40 amino acids, or in a particular embodiment at least 12 amino acids. In a particular embodiment, said system comprises a gamma-secretase complex and a peptide fragment SEQ ID NO: 2 [APP-C99] or a homologue with 95% identity thereof. In a further embodiment, said system comprises a gamma-secretase complex and a peptide fragment SEQ ID NO: 3 [A$\beta^{46}$] or a homologue with 95% identity thereof. Finally, in one embodiment, said system comprises a gamma-secretase complex and a peptide fragment constituting SEQ ID NO: 4 [A$\beta_{45}$] or a homologue with 95% identity thereof.

Other embodiments relate to said method wherein said quantification of A$\beta$ peptides comprises immune-based detection, while alternative embodiments relate to a method wherein said quantification of A$\beta$ peptides comprises mass spectrometry. Finally, in another embodiment, a method is provided wherein said quantification of A$\beta$ peptides comprises immune- and MS-based detection.

In an alternative embodiment, a method for producing a gamma-secretase stabilizing compound comprises the steps of a) providing a system comprising a gamma-secretase complex, and a substrate-like interactor (or APP-like interactor) of the gamma-secretase complex, or an inhibitor of gamma-secretase, b) administering a test compound to said system, and incubating said system in gamma-secretase complex-destabilizing conditions, and c) quantification of the binding interaction between said gamma-secretase complex and said substrate-like interactor in said system, wherein, under the same test conditions as compared to the same system without the test compound, an increase in the binding affinity identifies said test compound as a gamma-secretase stabilizing compound.

In more specific embodiments, said gamma-secretase complex-destabilizing conditions of said system are provided by incubation of said system at one or more temperature(s) in the range of about 35° C. to about 65° C., or alternatively, by incubation in the presence of a detergent added to the system.

DESCRIPTION OF THE FIGURES

The patent or application file contains at least one drawing executed in color. Copies of this patent or patent application publication with color drawing(s) will be provided by the Office upon request and payment of the necessary fee.

The drawings described are only schematic and are non-limiting. In the drawings, the size of some of the elements may be exaggerated and not drawn on scale for illustrative purposes.

A) Chemical structures of γ-secretase modulators used in the study. B-C) In vitro thermo-activity assays with purified wild type γ-secretase and wild type C99-3xFLAG in presence of direct (GSM(A), GSM(B)) or inverse GSM C (Fenofibrate). B) Direct modulators enhance γ-cleavage efficiency over temperatures ranging from 37 to 55° C., relative to DMSO control, (mean±SEM, n=4). Notice the 2× and 8× increase of the $4^{th}$ cycle with GSM A and GSM B respectively at 37° C. C) The stabilizing/destabilizing effects of GSMs are also observed at the first endoproteolytic cleavage of C99. The graph shows Gaussian fitting on AICD product levels, (mean±SEM, n=4; *,  and ** indicate $p_{values}$≤0.05, 0.01, and 0.0001, respectively).

Figure 6:
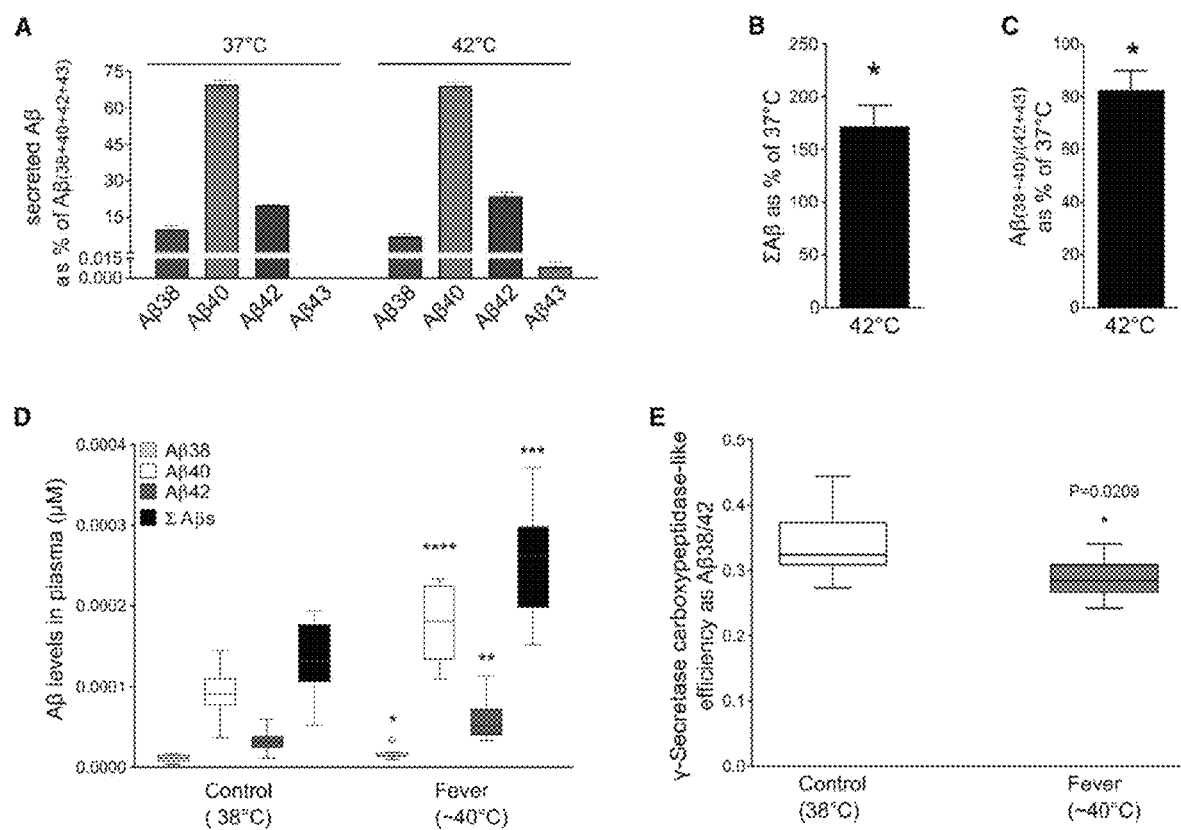

FIG. 6. Elevation in body temperature to fever range modulates γ-secretase activity on A-C) cultured cells and D-E) in viva A) ELISA quantified Aβ peptides secreted by HEK/Swe APP at 37° C. and 42° C.; B) Secreted $A\beta(\Sigma A\beta_{38}+A\beta_{40}+A\beta_{42}+A\beta_{43})$ and C) $(A\beta_{38}+A\beta_{40})/(A\beta_{42}+A\beta_{43})$ (products/substrates of the $4^{th}$ turnovers) ratio demonstrate increased Aβ secretion but decreased processivity at 42° C., relative to 37° C.; (Unpaired t-tests, *p≤0.05). D-E) Fever was induced in APP NL female mice by intraperitoneal injection of 30 µg of LPS and housing in a pre-warmed cage (see FIG. 11). D) Tukey box-and-whiskers plots for D) ELISA quantified Aβ steady-state levels in plasma and E) for protease efficiency at the $4^{th}$ catalytic turnover ($A\beta_{38/42}$ ratio) show increased secreted $\Sigma A\beta(A\beta_{38}+A\beta_{40}+A\beta_{42})$ levels and a significant reduction in the fever group after 100 min fever period, respectively. 10 control and 10 treated animals were tested, Unpaired two tailed t-tests, *, , * and **** indicate $p_{values}$≤0.05, 0.01, 0.001 and 0.0001, respectively.

Figure 7:
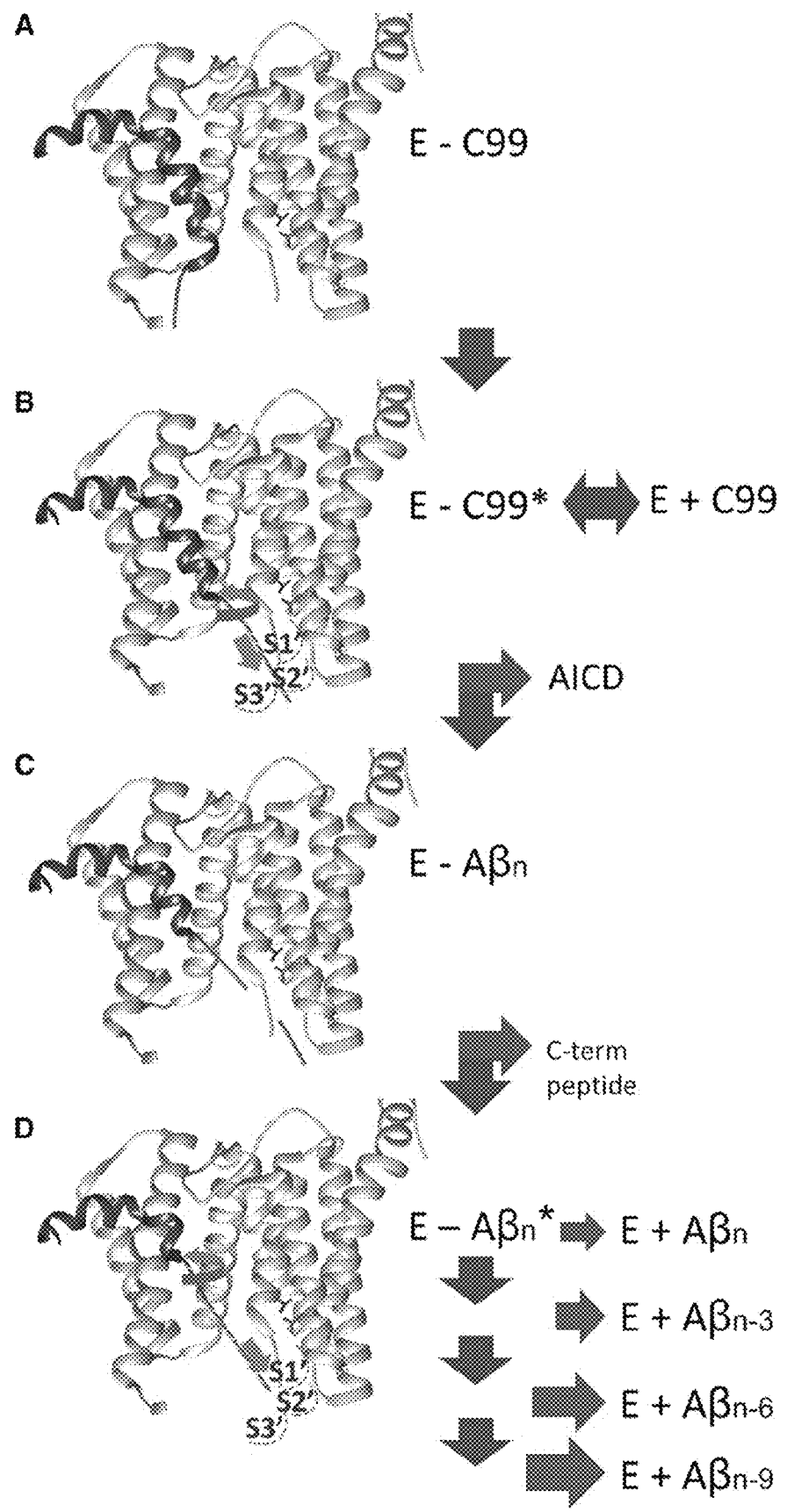

FIG. 7. Model for E-S interactions during the multiple turnover processing of APP by γ-secretase Lateral view of the 3D-PSEN1 structure (brown) (PDB: 5fn2, (Bai et al., 2015b)) with the structure of the $APP_{C99}$ substrate (in purple) (PDB:2LP1, (Barrett et al., 2012)) manually docked in the putative substrate binding (see FIG. 8 A4). A) C99 or C) $A\beta_n$ interacts with PSEN before it engages in the next catalytic cycle (E-S*) or is released (E+S) (B-D). Unwinding of the N-terminal transmembrane helix (B, D) occurs in order to fill the S1'-S3' enzyme pockets (Bolduc et al., 2016) during the next transition state. The progressive shortening of the N-terminal anchor progressively destabilizes γ-secretase-$A\beta_n$ complexes shifting the equilibrium towards dissociation (release of $A\beta_n$) (red arrows). Elevated temperature, FAD-linked mutations and exogenous compounds impact labile intermediate E-S complexes and enhance their dissociation (release of amyloidogenic Aβ) (red arrows).

Figure 8:
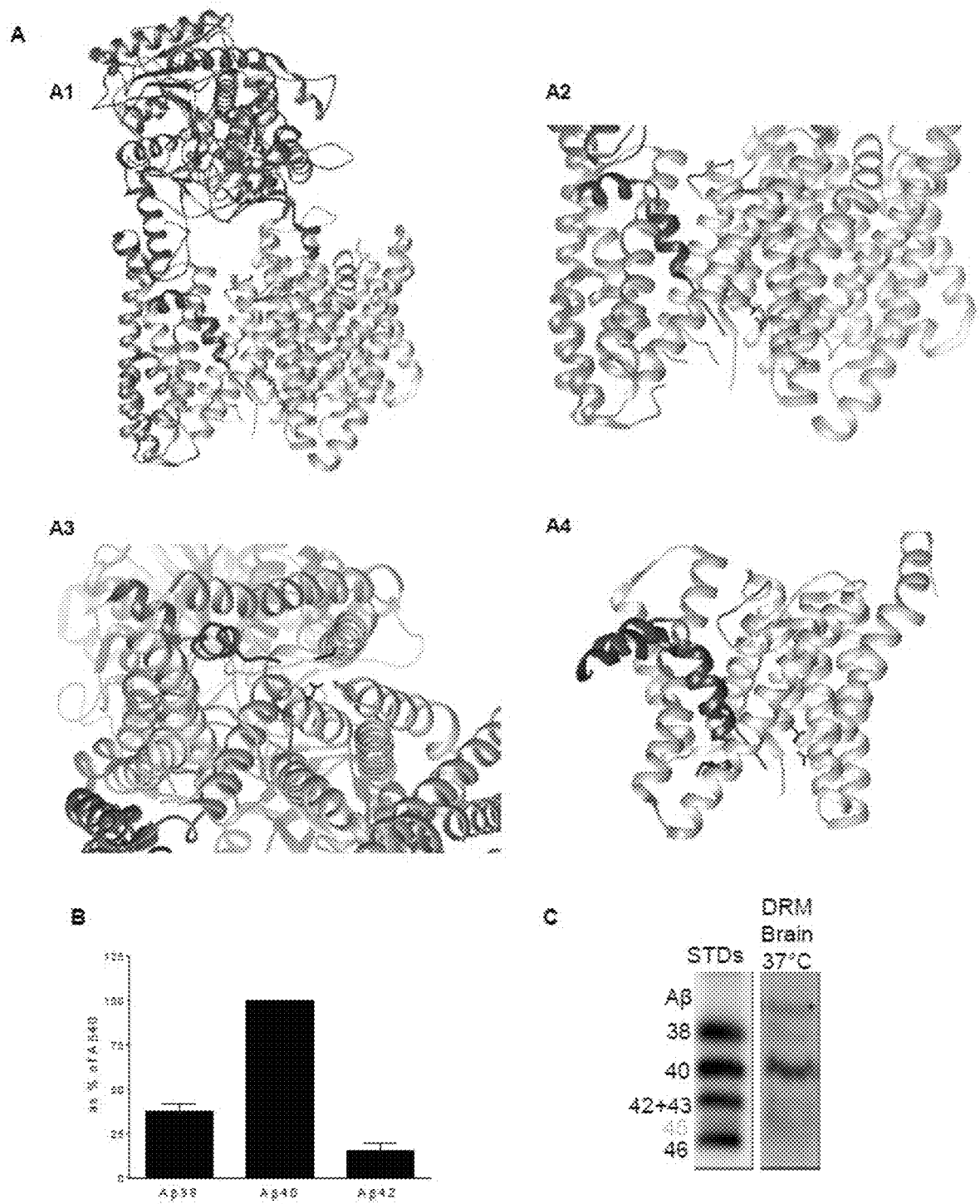

FIG. 8. 3D structure of human γ-secretase (PSEN1/APH1a) and its processivity

A1) 3D structure of the wild type human γ-secretase (PSEN1/APH1a) in complex with the putative substrate (PDB: 5fn2, Bai et al., 2015)). NCT in green, APH1 in yellow, PEN2 in brown, PSEN in beige and the putative substrate peptide in red. A2) lateral and A3) bottom views of the membrane core and A4) manual docking of the $APP_{C99}$ substrate (purple) (2LP1, Barrett et al., 2012)) into the putative substrate binding pocket of the γ-secretase complex.

B-C) DRMs prepared from human control brain samples tested in in vitro activity assays using 1.5 µM purified wild type APP$_{C99}$-3xFLAG substrate. ELISA quantifications and analysis of Aβ product profiles in urea-based gels show enhanced γ-secretase processivity (relative to detergent solubilized conditions (FIG. 1C, 37° C.)). Aβ$_{40}$ is the main product, similar to profiles generated in cell-based assays. The results support a stabilizing effect of the membrane environment. STDs, Standards.

Figure 9:
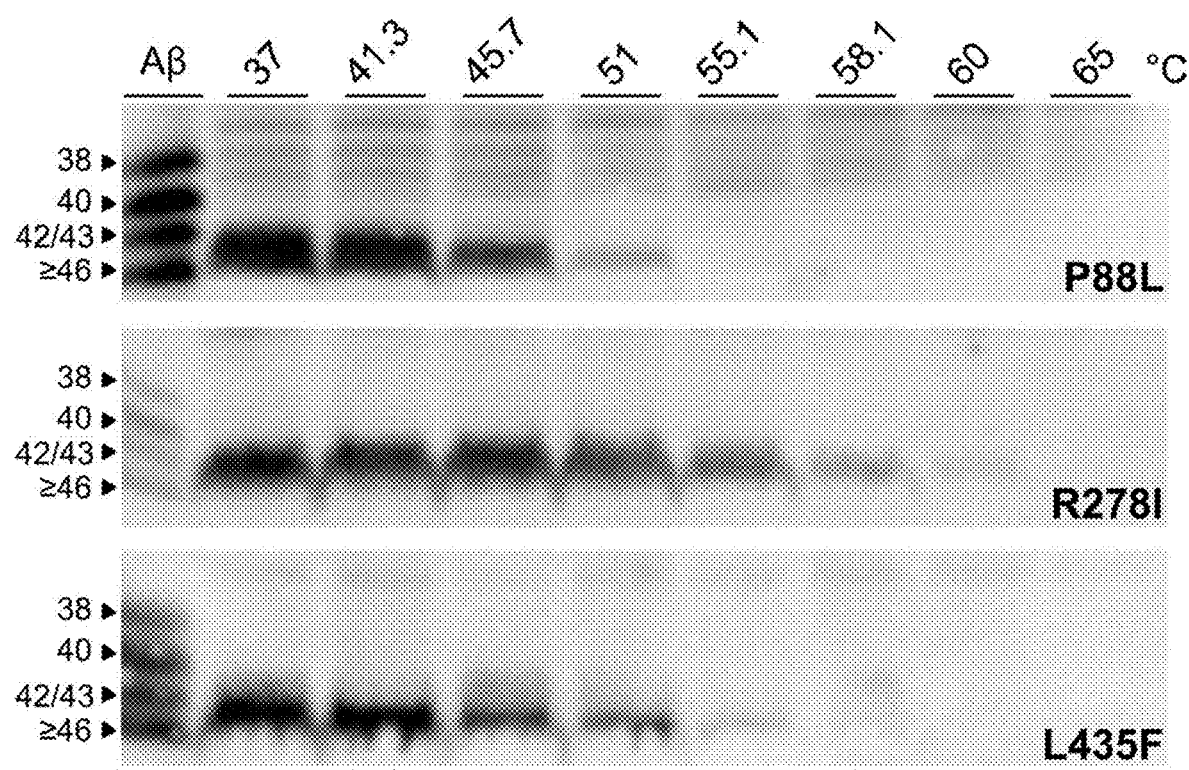

FIG. 9. Thermo-activity assays using PSEN1 mutants

Activity assays performed with purified γ-secretase complexes, containing P88L-, R278I- or L435F-PSEN1 pathogenic variants over a temperature gradient. Urea-based gel electrophoresis confirms production of only long Aβ peptides (≥Aβ$_{43}$) from this protease complexes at 37° C. (Ohki et al., 2014; Saito et al., 2011; Veugelen et al., 2016).

Figure 10:
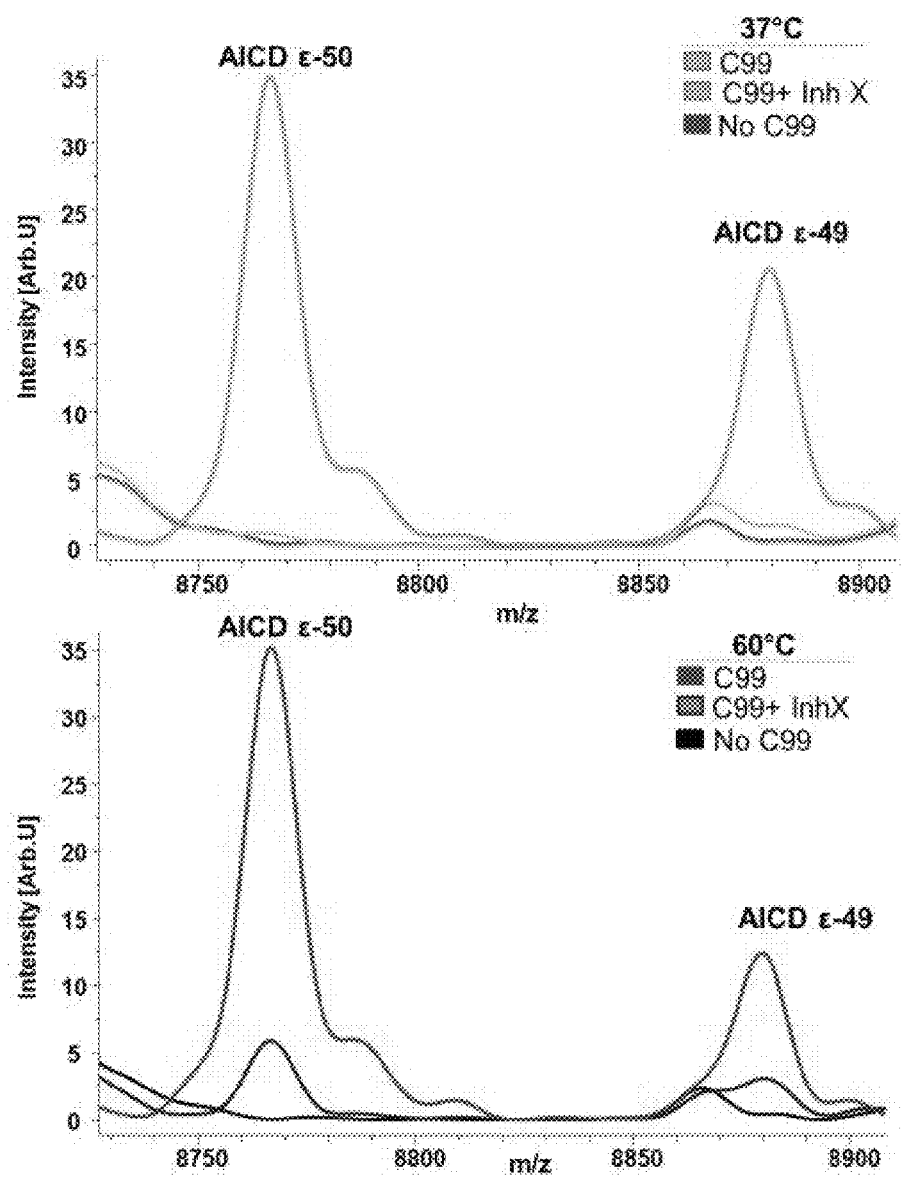
Figure 10:
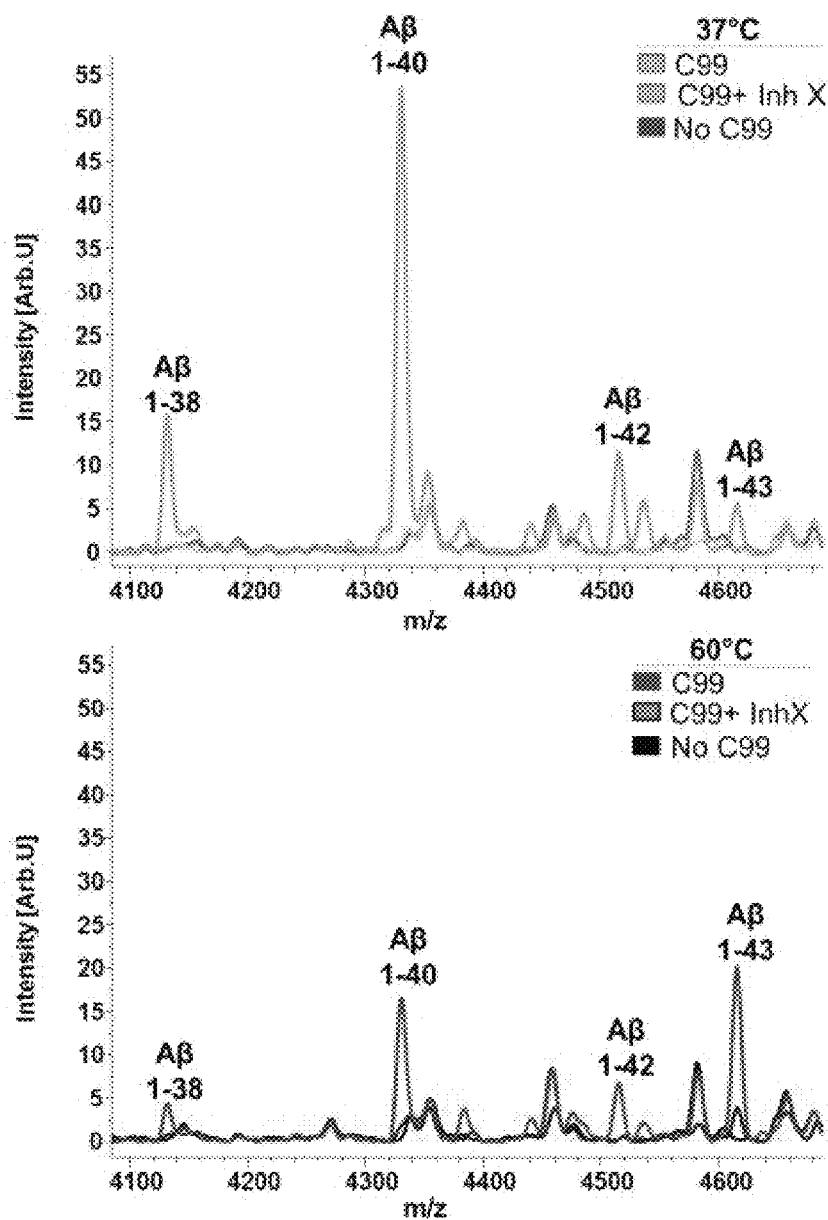
Figure 10:
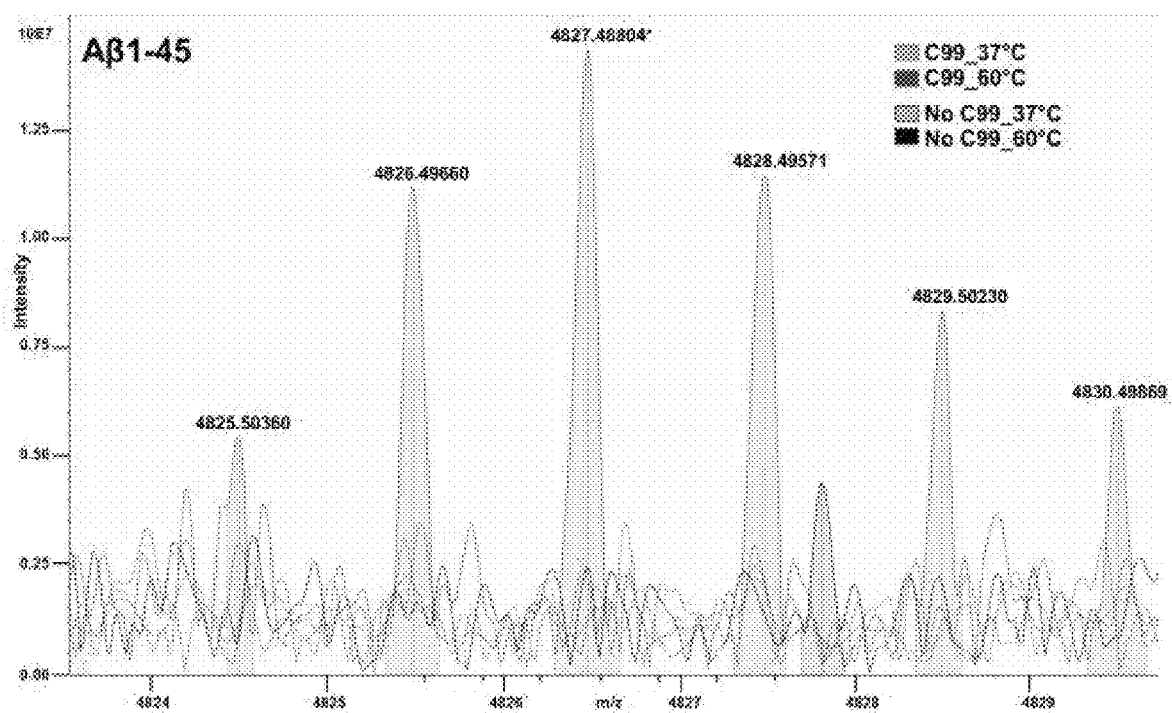
Figure 10:
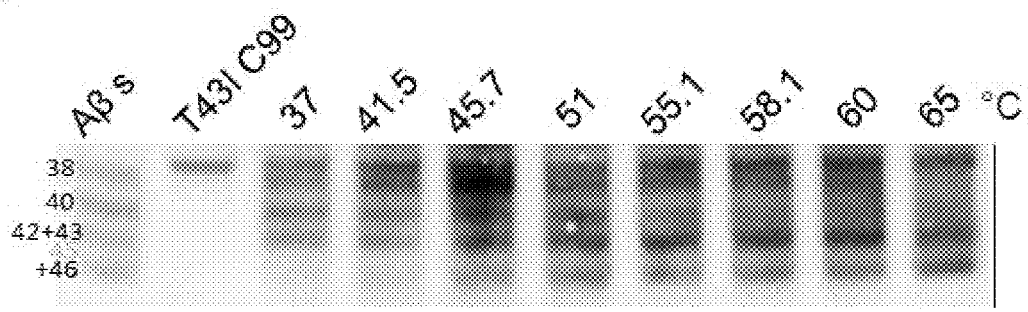
Figure 10:
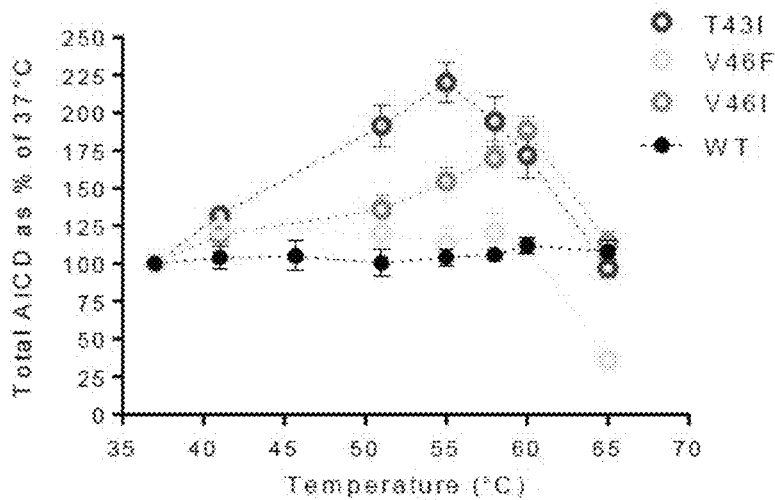
Figure 10:
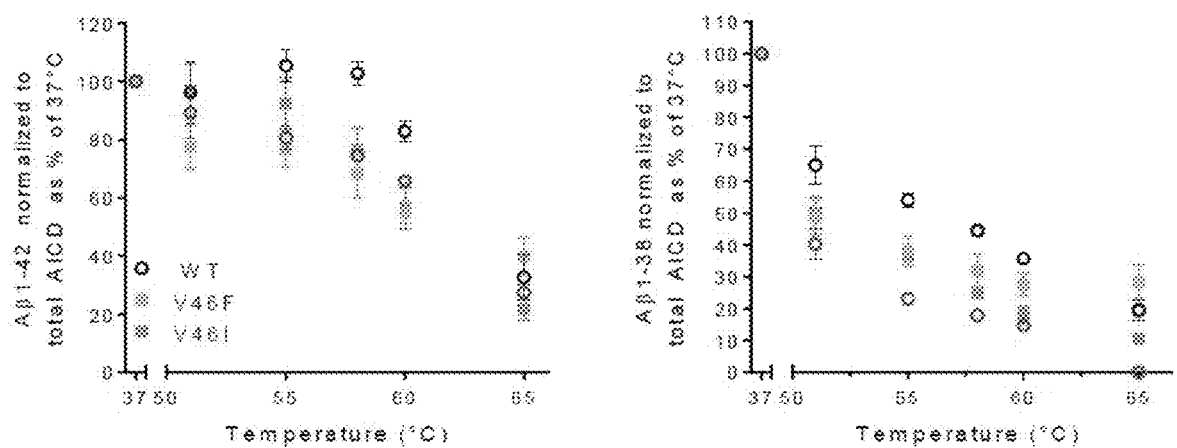
Figure 10:
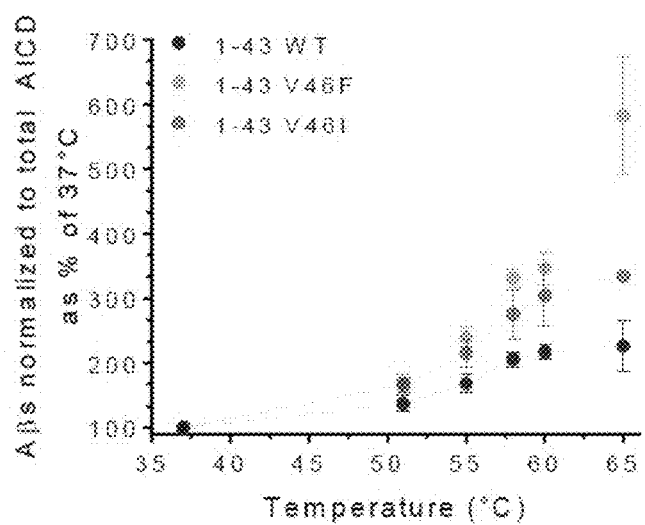

FIG. 10. MS-based MALDI mass spectrometry allows detection (and relative quantification) of the two (or more) alternative ε-cleavage products (AICD$_{50}$ and AICD$_{49}$) as well as the Aβ$_{38}$, Aβ$_{40}$, Aβ$_{42}$, Aβ$_{43}$ and Aβ$_{45}$ peptides, substrates and products of the $3^{rd}$ and $4^{th}$ γ-secretase turnovers in both amyloid product lines.

Figure 1:
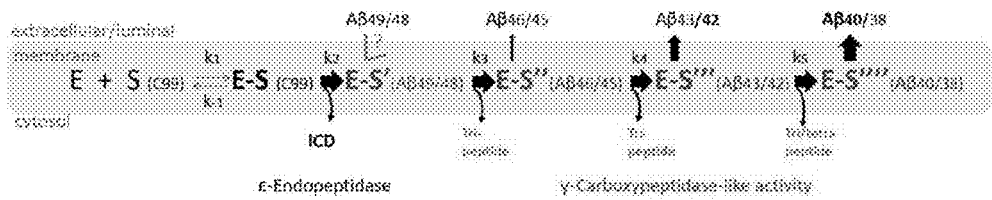
FIG. 1. Temperature increment induces production of "pathogenic-like" A$\beta$ profiles by wild type $\gamma$-secretase A) Schematic representation of the distinct Enzyme-Substrate (E-S) complexes characterizing the processing of APP by $\gamma$-secretase. B-E) In vitro activity assays with purified wild type human $\gamma$-secretase (PSEN1/APH1a) and APP$_{C99}$-3xFLAG at saturating concentration over a temperature gradient. B) Total AICD-3xFLAG product levels analyzed by quantitative western immunoblot (top panel) reveal similar AICD product levels (100±15%) in temperatures ranging from 37 to 55.1° C. (white background lower panel). Gaussian fitting indicates an optimal AICD production temperature of 44.8° C.±0.6° C. for AICD, (mean±SE, n>5). C) A$\beta$ profiles resolved in urea gels show enhanced generation of long A$\beta$ peptides in the 37 to 60° C. temperature range. Loading order: synthetic A$\beta$ peptides (A$\beta_{1-38}$, A$\beta_{1-40}$, A$\beta_{1-42}$, A$\beta_{1-45}$ and A$\beta_{1-46}$ peptides at 1/1/1/0.1/1 molar ratios), purified C99 substrate and proteolytic reactions incubated at indicated temperatures. D) A$\beta_{38}$, A$\beta_{40}$, A$\beta_{42}$ and A$\beta_{43}$ product levels were quantified by ELISA. Enzyme processivity estimated by the A$\beta_{40/43}$ and A$\beta_{38/42}$ ratios (substrate/product of the 4$^{th}$ turnover) reveal progressive reductions in the corresponding catalytic efficiencies over the 37° C.-51° C. range. E) Gaussian fit on temperature-induced decays of A$\beta_{38}$, A$\beta_{40}$, A$\beta_{42}$ and A$\beta_{43}$ products reveal a correlation between the optimal temperature of production (interpolated, vertical lines) and peptide length (maximal interpolated A$\beta$ levels adjusted to 100%; mean±SEM, n=4). F) $\gamma$-Secretase endopeptidase (E) and carboxypeptidase-like ($\gamma$) cleavage sites on transmembrane domains of APP (Takami et al., 2009) or Notch1 substrates (Okochi et al., 2006) (black and grey arrows on APP describe the two production pathways shown in FIG. 1A). G) Thermo-activity assays with purified wild type $\gamma$-secretase show similar temperature inactivating trends for Notch-3xFLAG (data in red) (mean±SD, n=3) and APP$_{C99}$-3xFLAG (data in gray, FIG. 1B). Dotted line indicates the corresponding Tm values, the temperature at which AICD or NICD production reaches 50% of their initial levels at 37° C. H-I) In vitro activity assays using DRMs prepared from four postmortem human brain samples and APP$_{C99}$-3xFLAG as substrate were incubated over a temperature gradient. H) De novo AICD levels determined by quantitative western blot (top panel) show no significant changes over the 37° C.-55° C. temperature interval (mean of means±SD, 4 patient samples, n=2). I) ELISA quantified A$\beta_{38}$ and A$\beta_{42}$ products demonstrate that increments in temperature lead to progressive impairment in $\gamma$-processivity, specifically at the 4$^{th}$ catalytic turnover; (mean of means±SD, 4 patient samples, n=2). Previously published A$\beta_{38/42}$ ratios (Szaruga et al., 2015) were determined at 37° C. for DRMs prepared from post-mortem brain samples of 22 FAD patients carrying 9 different mutations in PSEN (grey area, mean of means±SD). Std, Artificial Standard.
Figure 1:
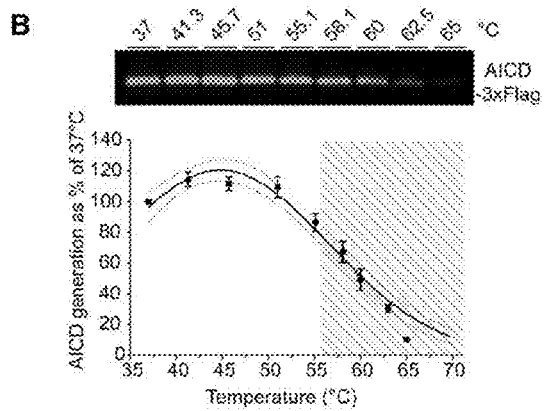
Figure 1:
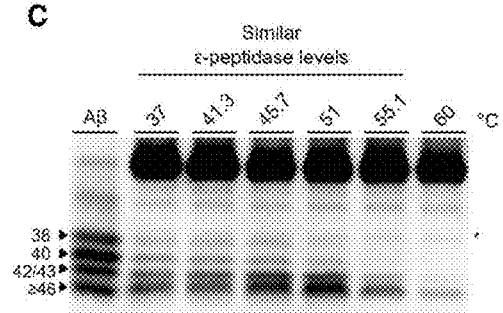
Figure 1:
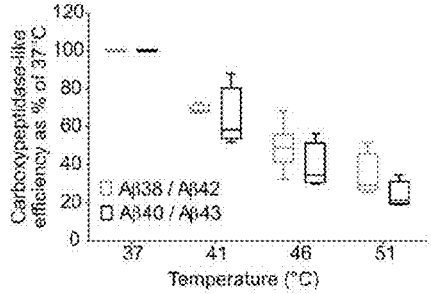
Figure 1:
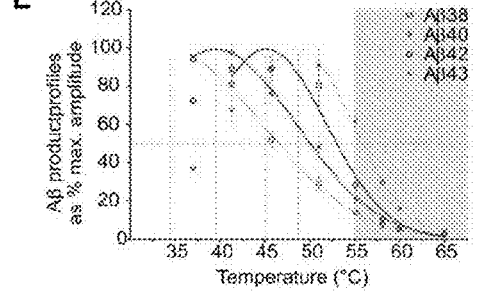
Figure 1:
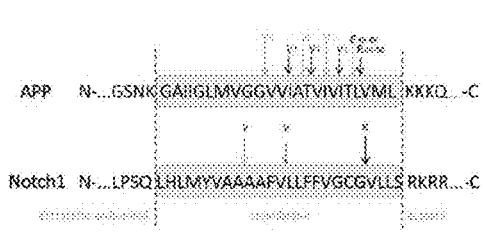
Figure 1:
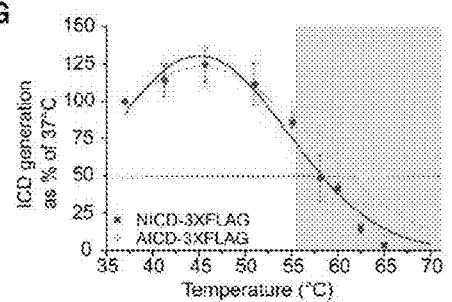
Figure 1:
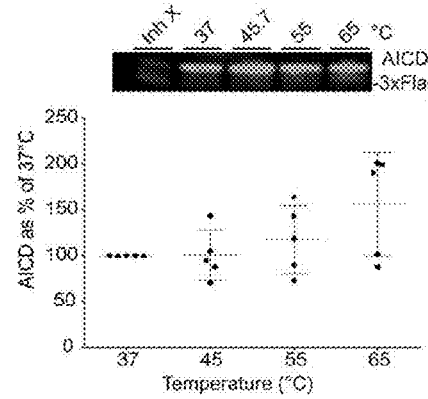
Figure 1:
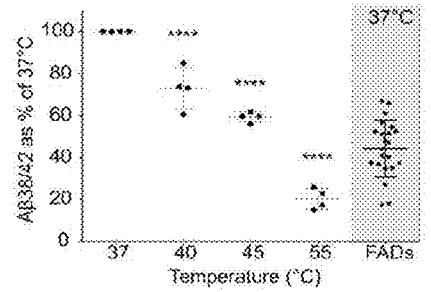
Figure 4:
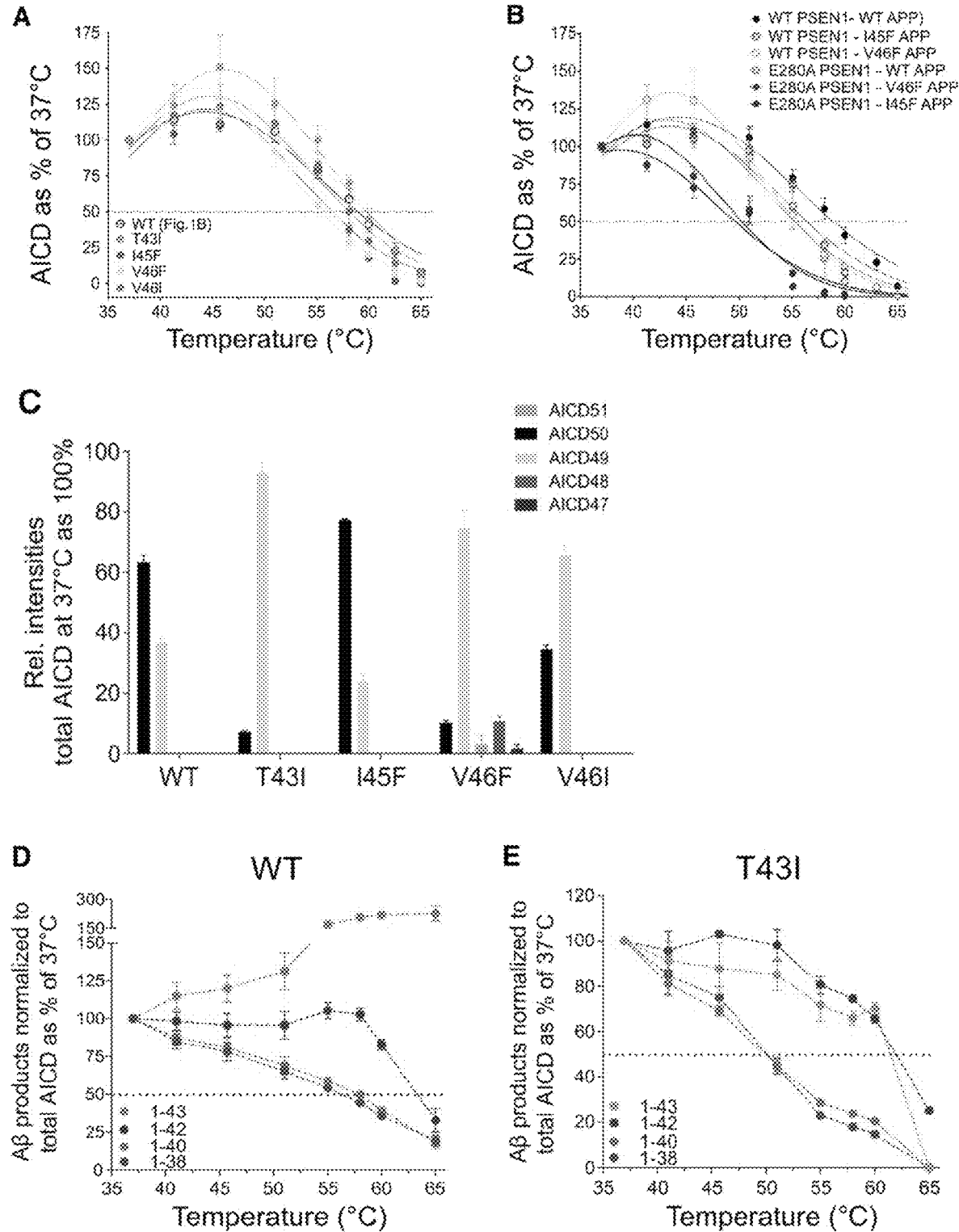
FIG. 4. AD-linked APP mutants consistently affect the stability of γ-E-S complexes AICD product levels generated in thermo-activity assays from the indicated mutant $APP_{C99}$-3XFLAG substrates and purified A) wild type or B) E280A-PSEN1 mutant γ-secretase complexes. Gaussian fittings on de novo AICD-3XFLAG levels (mean±SEM, nn). Dotted lines indicate the corresponding Tm values. C-H) MALDI-TOF Mass spectrometry analysis of thermo-activity assays using DRMs associated wild type γ-secretase complex and purified wild type or mutant $APP_{C99}$-3xFLAG substrates. C) De novo AICD products at 37° C.; (mean±SEM, n≥4, except for I45F mean±SD, n=2) and D-H) Aβ products generated from the indicated APP substrate over the indicated temperature gradient. Aβ product levels are normalized to total endopeptidase activity (total AICD levels); (mean±SEM, n≥4, except for I45F mean±SD, n=2). Dotted lines indicate the corresponding Tm values. I) $A\beta_{40}/A\beta_{43}$ ratios determined by ELISA in the extracellular media of HEK293 cells transiently expressing wild type or mutant APP substrates (n=4, one-way ANOVA and Dunnett's post-test, *** p≤0.001). J) Aβ product profiles generated at 37° C. and 55° C. resolved in urea-based gels. Synthetic $A\beta_{1-38}$, $A\beta_{1-40}$, $A\beta_{1-42}$, $A\beta_{1-45}$ and $A\beta_{1-46}$ peptides mixed at 1/1/1/0.1/1 molar ratios were loaded as reference.
Figure 4:
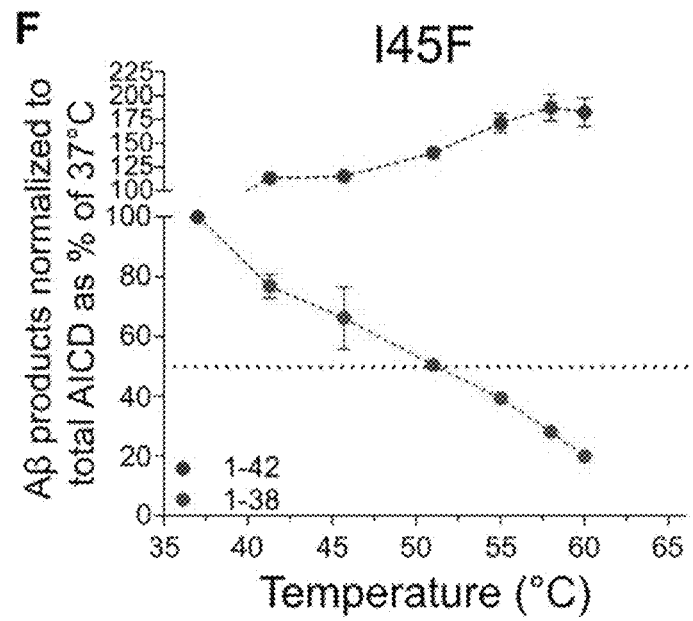
Figure 4:
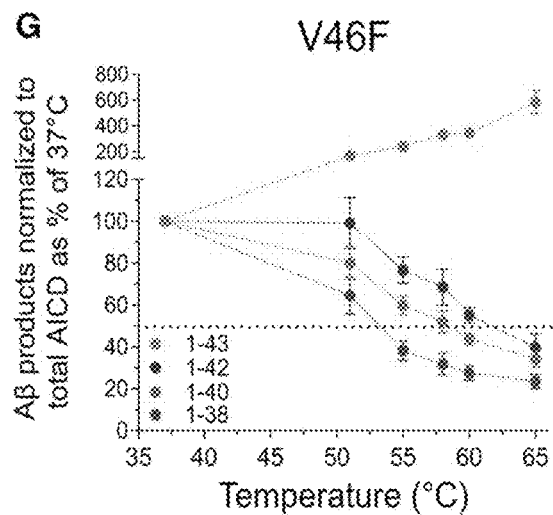
Figure 4:
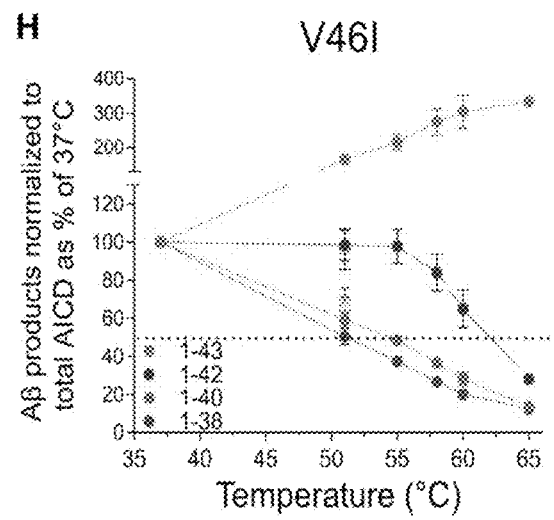
Figure 4:
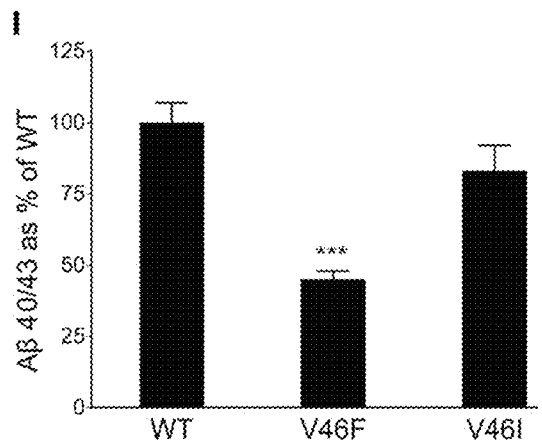
Figure 4:
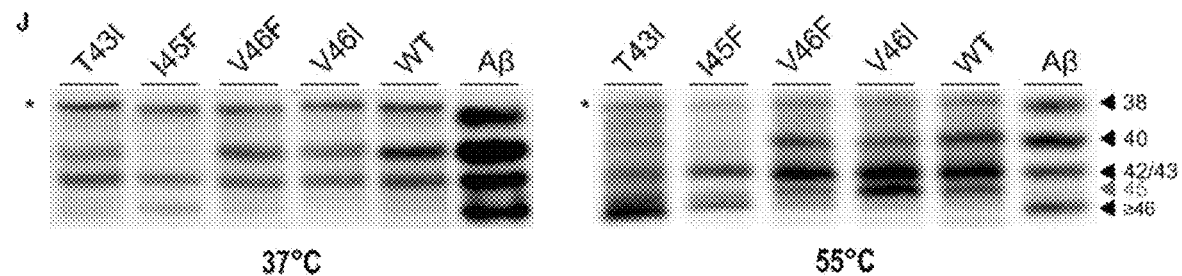

A-B) Illustrates the linear mode (low resolution) MALDI-TOF MS analysis of the AICD and Aβ peptide products generated by DRM-associated wild type γ-secretase from purified wild type APP$_{C99}$-3XFLAG in 20 min, at 37° C. (upper panel) or 60° C. (lower panel) in the presence or absence of the active site inhibitor X (Inh X). "No C99" denotes a no-substrate control reaction. C) Illustrates high resolution MALDI FT-ICR mass spectra of wild type Aβ$_{1-45}$ originating from APP$_{C99}$-3XFLAG in 20 min at 37° C. or 60° C. The high resolution analysis allows the monoisotopic separation of the target peptide with a mass accuracy of ~1 ppm calculated from the base peak (most intensive isotope, marked with a star *). "No C99" denotes a no-substrate control reaction. Please note that relative reductions in Aβ$_{38}$, Aβ$_{40}$ and Aβ$_{42}$ product levels are accompanied by increases in Aβ$_{43}$ and Aβ$_{45}$. E) MALDI-TOF MS analysis of the AICD products generated by (insect cells-derived) DRM-associated wild type human γ-secretase from either purified wild type or mutant APP$_{C99}$-3XFLAG at different temperatures. Note the increased temperatures compared to the experiments performed with detergent-solubilized enzyme (FIGS. 1B and 4A). Graphs show mean±SEM, n=4. D) DRMs prepared from insect cells expressing the wild type human γ-secretase were used as source of enzyme and tested in in vitro thermo-activity assays using purified mutant T43I APP$_{C99}$-3xFLAG substrate. Aβ profiles resolved in urea gels show enhanced generation of long Aβ peptides in the 37 to 60° C. temperature range. Loading order: synthetic Aβ peptides (Aβ$_{1-38}$, Aβ$_{1-40}$, Aβ$_{1-42}$, Aβ$_{1-45}$ and Aβ$_{1-46}$ peptides at 1/1/1/0.1/1 molar ratios), purified T43I APP$_{C99}$-3xFLAG substrate and proteolytic reactions incubated at indicated temperatures. F-G) Aβ product signal intensities extracted from low resolution MALDI TOF data, generated from wild type or mutant APP substrates at the indicated temperature and normalized to total endopeptidase activity (total AICD levels); mean±SEM, n=4.

Figure 11:
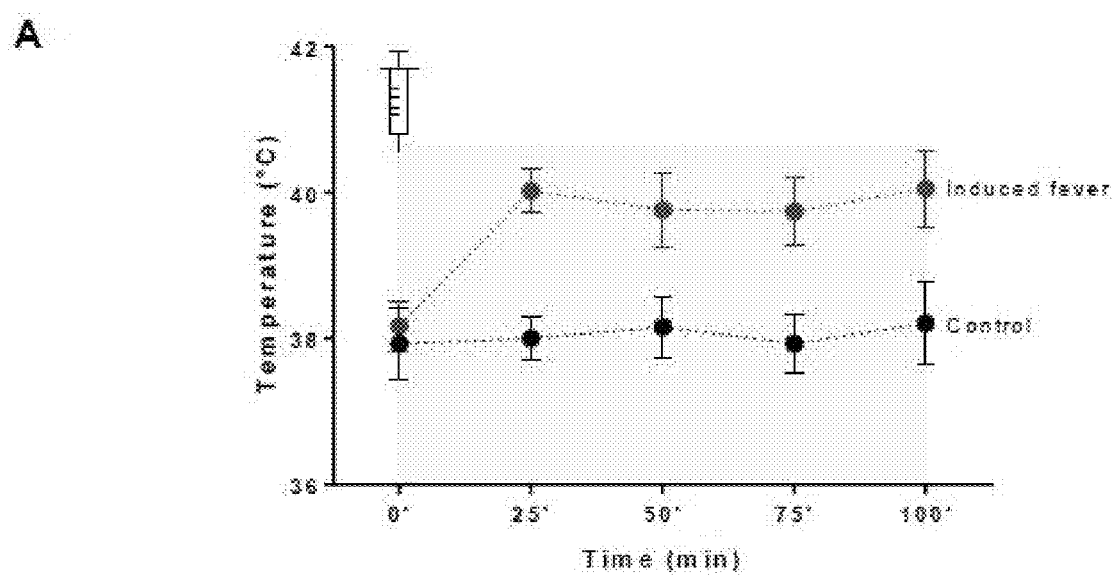

FIG. 11. Elevation in body temperature to fever range modulates γ-secretase activity in viva A) Fever was induced in APP NL female mice by intraperitoneal injection of 30 μg of LPS (syringe) and housing in a pre-warmed cage for 100 min. Control mice were kept at room temperature (RT, 22-24° C.) and subjected to the same handling. Mice body temperature was monitored by rectal measurements every 25 min. At the end of the experiment mice were sacrificed in CO2; mean of means±SD from 10 control and 10 treated animals.

DETAILED DESCRIPTION TO THE INVENTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, N.Y. (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "protein", "polypeptide", and "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes post-translational modifications of the polypeptide, such as glycosylation, phosphorylation and acetylation. By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

In a first aspect, the invention relates to a method for producing a gamma-secretase stabilizing compound comprising the steps of, a) providing a system comprising a gamma-secretase complex, and a protein SEQ ID NO:1 [APP] or a homologue with 95% amino acid identity thereof, or any fragment of SEQ ID NO:1, or any fragment of a homologue with 95% amino acid identity of SEQ ID NO:1, and b) administering a test compound to said system, and incubating said system in gamma-secretase complex-destabilizing conditions, and c) quantification of the Aβ peptides produced in said system, wherein, under the same test conditions as compared to the same system without the test compound, an increase in the ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ peptides identifies said test compound as a gamma-secretase stabilizing compound.

In one embodiment the method refers to a screening method and therefore possibly comprises a "high content screening (HCS)" of suitable test compounds. In some instances, HCS is a screening method that uses an in vitro system to perform a series of experiments as the basis for high throughput compound discovery. Typically, HCS is an automated system to enhance the throughput of the screening process. However, the present invention is not limited to the speed or automation of the screening process. In another embodiment of the invention, the HCS assay provides for a high throughput assay. Preferably, the assay provides automated screening of thousands of test compounds. The method is not limited to large or high-throughput or any scale, and can be refined based on the availability of test compounds or other variable features of the screening assay.

The method for producing a gamma-secretase-stabilizing compound comprises a first steps of, a) providing a system, wherein the term "system" comprises at least the necessary components and environment or conditions to execute said method. In one embodiment, said provided system is an in vitro system. An "in vitro system" makes use of biological molecules, organisms, a cell (or part of a cell) outside of their normal naturally-occurring environment, permitting a more detailed, more convenient, or more efficient analysis than can be done with whole organisms. "A buffer condition" or "condition" refers to the composition of the solution in which the assay is performed, and includes buffered solutions and/or solutes such as pH buffering substances, water, saline, physiological salt solutions, glycerol, preservatives, etc. for which a person skilled in the art is aware of the suitability to obtain optimal assay performance. Other aspects of the environment also influence the "conditions", such as pressure, temperature, optical density, among others. The in vitro system could also comprise liposomes (or proteoliposomes) or membranes wherein said gamma-secretase is reconstituted. In a particular embodiment, said in vitro system comprises a detergent resistant membrane preparation. Said detergent resistant membranes (DRMs) are applied as a tool in biochemical research of membrane proteins (Lingwood and Simons, 2007, Nature Protocols, vol 2: 2159). For instance, CHAPSO detergent resistant membranes (DRMs) can be prepared from human brain samples to isolate membrane fractions containing the gamma-secretase protein of interest, by fractionation via equilibrium density gradient centrifugation, after extraction from the tissue (see Example section). DRMs can also be prepared from insect cells overexpressing gamma-secretase proteins to use as a source of gamma-secretase protein in an in vitro system, for instance.

In another embodiment, said system is a cell-based system. A cell-based system comprises cells, and can be applied in vitro or in vivo. The skilled person in the art is aware of suitable cell-based systems. In the current application, Human embryonic kidney (HEK) cell culture is used as a system, but also other mammalian cell lines such as Chine Hamster Ovary (CHO) cells can be applied. In a particular embodiment, said system comprises an in vivo system. An "in vivo system" as used herein comprises a biological environment wherein the normal natural occurring environment provides conditions allowing the method to be executed. Examples of an in vivo system are neuronal cells or brain tissue, but also subjects such as a *Drosophila* fly, a mouse, a rodent, a rabbit, a cow, a sheep, a horse, a dog, a cat, a lama, a pig, or a non-human primate (e.g. a monkey). The method of the present invention requires conditions in which the gamma-secretase complex is capable to cleave the protein substrate within the environment, which may in addition be gamma-secretase complex-destabilizing conditions. Several parameters will influence the capacity or conditions of said system such as the pH, buffer composition, temperature, etc.

The invention relates to a screening method for quantification and detection of amyloid beta peptide products for identification of gamma-secretase stabilizing compounds. The accumulation of brain amyloid Aβs is the major pathological feature of Alzheimer's disease. The generation of A-beta (Aβ) from amyloid precursor protein (APP) is a complex process requiring successive cleavages by two proteases, beta-(β) and gamma-(γ) secretase, producing a carboxyl-terminal (C-terminal) fragment (CTF) consisting of 99 amino acids (C99/β-CTF). The APP C99 can be subsequently cleaved by gamma-secretase via epsilon (ε) and gamma (γ) cleavage activity within its transmembrane domain (TMD), generating Aβ and an intracellular fragment known as APP intracellular domain (AICD). These ε and γ cleavages occur near the middle and near the cytoplasmic face of the TMD, respectively. Some experimental evidence shows that gamma-secretase cleavage of gamma-secretase substrates, in particular of APP and Notch, occurs sequentially with the cleavage at epsilon preceding cleavage at gamma. Gamma-secretase is a multi-subunit aspartyl protease that is biologically and biochemically heterogeneous, and typically consists of at least four different membrane proteins, Presenilin 1 or 2 (PSEN1/2), Nicastrin (NCT), Anterior Pharynx Defective 1 (Aph-1) A or B and Presenilin enhancer 2 (Pen2). PSEN is the catalytic core of the holoenzyme, containing two conserved intramembrane aspartate residues essential for substrate cleavage. The precise mechanisms by which gamma-secretase recognizes and cleaves its substrates remain elusive, partly because these proteolytic events occur within a hydrophobic environment of membrane lipid bilayer.

The terms "gamma-secretase", "gamma-secretase protein complex" and "gamma-secretase complex" refer to a protein complex used in the present invention comprising at least four protein molecules, where at least one of the protein molecules provides a catalytic site for cleavage of a polypeptide substrate having a gamma-secretase cleavage sequence, and wherein the protein molecules are PSEN1 or PSEN2, Aph1a or Aph1b, NCT, and/or PEN2. The protein molecules that comprise the gamma-secretase protein complex may associate with each other. Additionally, the gamma-secretase protein complex may also include non-proteinaceous molecules, such as vitamins, ATP, or divalent cations. Many mutations within one or more of said membrane proteins constituting the gamma-secretase complex are causal for amyloid beta generation and Alzheimer disease. Those clinically relevant mutants can be but are not per se loss of function mutants. For instance, different mutations in PSEN affect γ-secretase structure or function in multiple ways, such as PS1-D9 and PS1-L166P mutations causing a reduction in β-amyloid peptide Aβ$_{40}$ production whereas PS1-G384A mutant significantly increasing Aβ$_{42}$. In an alternative embodiment, said system of said method comprises a gamma-secretase complex wherein said protein complex comprises PSEN1/2, Aph1, NCT or PEN2 mutant subunits. The person skilled in the art is aware of those mutants with potential impact in gamma-secretase activity and clinical relevance in Alzheimer's Disease (AD). In a preferred embodiment, the gamma secretase complex provided in the system of step a) of the method comprises a pathogenic PSEN 1/2 mutant subunit, which will lead to a lower stability of the gamma-secretase complex and thereby to a lower processivity and faster release of Aβ peptides, resulting in longer and more amyloidogenic peptides as compared to using the wild type gamma-secretase complex. In fact, the application of PSEN 1/2 mutant subunits as part of the gamma-secretase complex induces by itself already gamma-secretase complex-destabilizing conditions required for step b) of the method of the invention.

In one embodiment, the invention relates to a method for producing a gamma-secretase-stabilizing compound comprising a first step of providing a system comprising a gamma-secretase complex, and a (poly)peptide SEQ ID NO:1 [APP] or a homologue with 95% amino acid identity to SEQ ID NO:1, or any fragment thereof. More particular, 'any fragment thereof' relates to any peptide with at least 12 consecutive amino acids, or at least 40 consecutive amino acids of the protein of SEQ ID NO:1. Alternatively, 'any fragment thereof' relates to any peptide with at least 12 consecutive amino acids, or at least 40 consecutive amino acids of a homologue with 95% identity to SEQ ID NO:1.

SEQ ID NO: 1 depicts the amino acid sequence of the human Amyloid beta precursor protein (APP) (isoform 695/695 aa).

SEQ ID NO: 1: Human Amyloid beta precursor protein (APP) protein sequence (695 aa):
MLPGLALLLLAAVVTARALEVPTDGNAGLLAEPQIAMFCGRLNMHMNVQN

GKWDSDPSGTKTCIDTKEGILQYCQEVYPELQITNVVEANQPVTIQNWCK

RGRKQCKTHPHFVIPYRCLVGEFVSDALLVPDKCKFLHQERMDVCETHLH

WHTVAKETCSEKSTNLHDYGMLLPCGIDKFRGVEFVCCPLAEESDNVDSA

DAEEDDSDVWWGGADTDYADGSEDKVVEVAEEEEVAEVEEEEADDDEDDE

DGDEVEEEAEEPYEEATERTTSIATTTTTTTESVEEVVRVPTTAASTPDA

VDKYLETPGDENEHAHFQKAKERLEAKHRERMSQVMREWEEAERQAKNLP

KADKKAVIQHFQEKVESLEQEAANERQQLVETHMARVEAMLNDRRRLALE

NYITALQAVPPRPRHVFNMLKKYVRAEQKDRQHTLKHFEHVRMVDPKKAA

QIRSQVMTHLRVIYERMNQSLSLLYNVPAVAEEIQDEVDELLQKEQNYSD

DVLANMISEPRISYGNDALMPSLTETKTTVELLPVNGEFSLDDLQPWHSF

GADSVPANTENEVEPVDARPAADRGLTTRPGSGLTNIKTEEISEVKMDAE

FRHDSGYEVHHQKLVFFAEDVGSNKGAIIGLMVGGVVIATVIVITLVMLK

KKQYTSIHHGVVEVDAAVTPEERHLSKMQQNGYENPTYKFFEQMQN

"Homologue" or "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. According to the present invention, the degree of amino acid identity between a given reference amino acid sequence or fragment thereof and an amino acid sequence which is a variant or mutant of said given amino acid sequence or said fragment thereof will preferably be at least about 95%, 96%, 97%, 98%, or 99%. The degree of identity is given preferably for an amino acid region which is at least about 90% or about 100% of the entire length of the reference amino acid sequence. For example, if the reference amino acid sequence consists of 200 amino acids, the degree of identity is given preferably for at least about 180, or about 200 amino acids, preferably continuous amino acids. In preferred embodiments, the degree/percentage of identity is given for the entire length of the reference amino acid sequence. In other embodiments, said fragments of the reference sequence with a degree of identity is referring to the degree/percentage of identity for said fragment wherein said fragment is aligned to the most optimally aligned region over the window of comparison of said reference sequence. The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. The alignment for determining sequence identity, can be done with art known tools, preferably using the best sequence alignment, for example, using CLC main Workbench (CLC bio) or Align, using standard settings, preferably EMBOSS::needle, Matrix: Blosum62, Gap Open 10.0, Gap Extend 0.5.

In a further particular embodiment, said method comprises as a first step providing a system comprising a gamma-secretase complex and a fragment of SEQ ID NO:1, said fragment constituting a peptide SEQ ID NO: 2 [APP-C99]. Alternatively, said method comprises a first step providing a system comprising a gamma-secretase complex and a fragment constituting a homologue with 95% identity to SEQ ID NO:2 [APP-C99]. SEQ ID NO: 2 depicts the amino acid sequence of the human Amyloid beta precursor protein C99 (APP-C99) (isoform 695/99aa).

```
SEQ ID NO: 2: Human Amyloid beta precursor protein
C99 (APP-C99) protein sequence (99 aa):
DAEFRHDSGYEVHHQKLVFFAEDVGSNKGAIIGLMVGGVVIATVIVITLV
MLKKKQYTSIHHGVVEVDAAVTPEERHLSKMQQNGYENPTYKFFEQMQN
```

In a further embodiment, said method comprises as a first step providing a system comprising a gamma-secretase complex and a fragment of SEQ ID NO:1, said fragment constituting a peptide SEQ ID NO: 3 [Aβ$_{46}$]. Alternatively, said method comprises as a first step providing a system comprising a gamma-secretase complex and a fragment constituting a homologue with 95% identity to SEQ ID NO: 3 [Aβ$_{46}$]. SEQ ID NO:3 depicts the amino acid sequence of the human Aβ46 fragment derived from APP.

```
SEQ ID NO: 3: Human Amyloid 46 fragment (Aβ46)
protein sequence (46 aa):
DAEFRHDSGYEVHHQKLVFFAEDVGSNKGAIIGLMVGGVVIATVIV
```

In another particular embodiment, said method comprises as a first step providing a system comprising a gamma-secretase complex and a fragment of SEQ ID NO:1, said fragment constituting a peptide SEQ ID NO: 4 [Aβ$_{45}$]. Alternatively, said method comprises as a first step providing a system comprising a gamma-secretase complex and a fragment constituting a homologue with 95% identity to SEQ ID NO:4 [Aβ$_{45}$]. SEQ ID NO:4 depicts the amino acid sequence of the human Aβ$_{45}$ fragment derived from APP.

```
SEQ ID NO: 4: Human Amyloid 45 fragment (Aβ45)
protein sequence (45 aa):
DAEFRHDSGYEVHHQKLVFFAEDVGSNKGAIIGLMVGGVVIATVI
```

Gamma-secretase complex proteins are actively cleaving or processing multiple other proteins or substrates. Some non-limiting examples of a gamma-secretase substrate include amyloid precursor protein (APP), Notch, amyloid precursor-like protein (APLP2), tyrosinase, CD44, erbB4, n-cadherin and SCNB2, and the like. Gamma-secretase substrates also include any isotypes (isoforms) of known gamma-secretase substrates. Further, gamma-secretase substrates are not limited to human sequences, but also include substrates from other mammals (orthologues), including mouse, rat, guinea pig, primates and the like. Said substrates can be synthetic, chimeric and/or recombinant polypeptides that can be processed by gamma-secretase, under conditions that allow for gamma-secretase activity. Those conditions can be optimal or sub-optimal for the enzymatic activity, and in particular, those conditions may be gamma-secretase complex-destabilizing conditions.

In one embodiment, the method comprises a system comprising gamma-secretase and amyloid precursor protein (APP), which is depicted in SEQ ID NO:1, and functioning as a substrate, since APP specifically leads to the production of amyloidogenic Aβ peptides resulting in aggregation at the onset of AD. The naturally occurring APP is processed by β-secretase activity to result in an APP fragment as APP-C99, as depicted in SEQ ID NO:2, which is a substrate for γ-secretase activity. Therefore, in alternative embodiments, any fragment of APP of at least 40 amino acids, or in particular of at least 12 amino acids is sufficient within said system of said method to act as a substrate for interaction with gamma-secretase present in said system of said method. Some APP substrate peptides can be expressed in a cell endogenously or recombinantly as transmembrane proteins or polypeptides. As used herein the term "Aβ peptide" means the N-terminal product from cleavage of gamma-secretase at the gamma cleavage site of the APP protein or APP fragment substrate.

Gamma-secretase is processing the APP substrate into Aβ peptides of different length (FIG. 1A). The shortest possible fragment to function as a substrate for said gamma-secretase complex comprised in said system is therefore minimally 40 amino acids, or looking into defined region of said fragments, even limiting the fragment length to a minimum of 12 consecutive amino acids. Theoretically, APP or any fragment thereof can function in said system to produce gamma-secretase stabilizing compounds. Therefore, in an alternative embodiment, said system comprises any fragment of SEQ ID NO:1 [APP] as a substrate for gamma-secretase. In one particular embodiment, the APP C99 fragment as preferred natural substrate is present in said system (i.e. SEQ ID NO:2), and comprises a juxtamembrane and transmembrane domain within the peptide sequence. Other embodiments comprise APP fragments with a length of 98 amino acids or less, even with a more preferred fragment size of 49, 48, 46, 45, 43, 42, or 40 amino acids, or even smaller defined region from said fragments, resulting in a minimal fragment length of 12 amino acids.

The (poly)peptide substrates that can be cleaved by the gamma-secretase complex may be generated by various methods. For example, the substrates may be isolated as a component of a membrane fraction from naturally-occurring sources, such as brain tissue samples or cell cultures. Alternatively, the substrates may be generated using recombinant DNA technology, and a host-vector system. The substrates may also be generated by chemical synthesis technology using the amino acid sequence of APP as a basis for synthesizing the polypeptide. The substrates may also be generated by in vitro transcription-translation methods. The preferred substrates are generated in a form that is surrounded by a membrane-like environment, such as a microsome membrane or a detergent that mimics a membrane-like environment (e.g. solubilized form). The substrates generated by any of these methods may be labelled with a detectable marker. Examples of a detectable marker include, but are not limited to, a radioisotope, a fluorescent compound, a bioluminescent compound, a chemiluminescent compound, a metal chelator or an enzyme. Technologies for generating labelled polypeptides and proteins are well known in the art.

In the current invention, it is demonstrated that Aβ substrate shortening progressively destabilizes the consecutive enzyme/substrate (E-S) complexes that characterize the sequential γ-secretase processing of APP. In the current invention, "gamma-secretase stabilizing compound" or "gamma-secretase substrate stabilizing compound" or "GSSC" is used interchangeably and refers to a compound which, upon administration of said compound to said system comprising the gamma-secretase and said APP/Aβ substrate, provides an increased stability of the enzyme/substrate complex, as compared to the same test conditions without administered compound. "Compound" or "test compound"

means any chemical or biological compound, including simple or complex organic and inorganic molecules, peptides, peptidomimetics, proteins, antibodies, carbohydrates, nucleic acids or derivatives thereof. The term "compound" is used herein in the context of a "drug candidate compound" or a "candidate compound for Lead optimization" in therapeutics, described as identified with the screening methods of the present invention. The term "small molecule compound", as used herein, refers to a low molecular weight (e.g., <900 Da or <500 Da) organic compound. The compounds also include polynucleotides, lipids or hormone analogues that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates.

With "increased stability", it is meant that the enzyme/substrate complex has a longer half-life, higher melting temperature (Tm), improved binding properties, and/or more efficient processing of Aβ cleavage. "Increased" stability refers to a change compared to the control in the absence of the compound, preferably, but not by way of limitation, at least of about 5%, at least of about 10%, at least of about 15%, at least of about 20%, at least of about 25%, at least of about 30%, at least of about 35%, at least of about 40%, at least of about 45%, at least of about 50%, at least of about 60%, at least of about 70%, at least of about 80%, or at least of about >90%. More specifically, the higher the enzyme/substrate complex its (thermo)stability, the better its processivity to cleave substrate, hence, the higher the resulting amount of shorter Aβ peptides. Tm also shifts for production of AICD, $A\beta_{38}$, $A\beta_{40}$, $A\beta_{42}$ production when gamma-secretase substrate stability is altered. Remarkably, pathogenic PSEN or APP mutations further destabilize labile E-S complexes and thereby promote generation of longer Aβ peptides. Similarly, destabilization of wild type E-S complexes by temperature, compounds, or detergent promotes release of amyloidogenic Aβ. In addition, several FAD-causing APP mutations, known to affect the γ-secretase processivity of APP, destabilize the E-S interaction and prime "de novo long Aβ substrates" for dissociation. In contrast, the invention presents γ-secretase modulators (GSMs) that increase enzyme processivity by stabilizing E-S interactions upon increased temperatures, called gamma-secretase stabilizing compounds (GSSC). These data provide a unifying and coherent explanation for how FAD causative mutations affect γ-secretase processivity. Of importance for sporadic AD, fever range temperature- or exogenous compound-induced destabilization of wild type γ-secretase-substrate complexes in vitro and in vivo is sufficient to produce amyloidogenic Aβ peptides, which mimics an FAD-like effect.

In one embodiment, said gamma-secretase stabilizing compound is produced by a method comprising a step of quantification of the Aβ peptides produced in said system, wherein, under the same test conditions as compared to the same system without the test compound, an increase in the ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ peptides identifies said test compound as a gamma-secretase stabilizing compound. Said ratio is determined by the reaction efficiency of the substrate to product conversion of the $4^{th}$ turnover of gamma-secretase as shown in FIG. 1A. In one embodiment, an increase in the ratio of $A\beta_{38}/A\beta_{42}$ peptides will be determined, while in an alternative embodiment a ratio of $A\beta_{40}/A\beta_{43}$ will be determined, and in another embodiment the ratio of $A\beta_{40}/A\beta_{42}$ will be defined, and finally, also the sum of the "shorter" and "longer" peptides is provided by $A\beta_{(38+40)}/A\beta_{(42+43)}$. When an increased ratio is obtained, the resulting amount of shorter Aβ peptides will be higher than the resulting amount of "less-processed" or longer Aβ peptides, which indicates that the gamma-secretase substrate complex was more active, and therefore showing increased (thermo)stability.

In one embodiment, said method for producing a gamma-secretase stabilizing compound comprises the steps of providing a system comprising gamma-secretase complex, and a substrate [APP/Aβ] or a 95% identity homologue or fragment of said substrate [APP/Aβ], or a fragment of said 95% identity homologue; administering a test compound to said system, and incubating said system at a temperature in the range of about 35° C. to about 65° C.; and a step comprising quantification of the Aβ peptides to identify GSSCs as compound with an increased ratio of $A\beta_{38}/A\beta_{42}$ or of $A\beta_{40}/A\beta_{43}$ or of $A\beta_{40}/A\beta_{42}$ or of $(A\beta_{38}+A\beta_{40}/(A\beta_{42}+A\beta_{43})$ as compared to the controls. Said "temperature range of about 35° C. to about 65° C." forms the key to screen for a compound altering the thermostability of the enzyme/substrate complex active within said system. The higher the thermostability, i.e. the processing activity upon increasing temperature, the higher the cleavage activity of the gamma-secretase, and the higher the amount of "shorter" Aβ peptides (i.e. $A\beta_{38}$ and $A\beta_{40}$) versus the amount of non- or partially-processed "longer" Aβ peptides (i.e. $A\beta_{42}$, $A\beta_{43}$ and longer fragments of APP). Upon increased temperatures, the test compound that is identified in said method as a GSSC will lead to an increased $A\beta_{38}/A\beta_{42}$ and/or $A\beta_{40}/A\beta_{43}$ and/or $A\beta_{40}/A\beta_{42}$ and/or $(A\beta_{38}+A\beta_{40})/(A\beta_{42}+A\beta_{43})$ ratio as compared to the controls, and said increase will become more distinct from the controls with increasing temperature. As of 35° C., which is close to the 37° C. human body temperature, the difference is detectable for the most active GSSC compounds or in the most optimal system of said method. With "optimal" system is meant the combination of the most active gamma-secretase subunits, the most suitable APP/β substrate, and the best conditions for allowing cleavage activity. Elevated temperatures within a range of about 35° C. to about 55° C. were demonstrated to not significantly impair E-peptidase cleavage. Hence said range of 35° C. to about 55° C. will allow to screen for compounds that stabilize the gamma-secretase substrate complex most effectively, hence also in "sub-optimal" systems or even in "gamma-secretase complex-destabilizing conditions". With sub-optimal systems is meant for instance that less active gamma-secretase subunit polypeptides are used (isoform, variant, mutant) or APP mutants that are already destabilizing the complex, shorter Aβ forms (i.e. <45 aa) which form less optimal substrates (see Example section), or is meant less optimal conditions, such as a deviating pH, less optimal buffer, detergents or denaturing agents, etc. In a particular embodiment, the incubation of said system at a temperature in the range of about 37° C. to about 55° C. is used to produce GSSC compounds with said method.

In an alternative embodiment, a screening method for producing gamma-secretase stabilizing compounds comprising said steps, wherein said incubation at a temperature range of about 35° C. to about 65° C. is performed by selecting a number of temperature conditions to incubate (replicate) samples, or the system, followed by Aβ quantification analysis. A non-limiting example is comprising samples or said system being incubated at 37° C., at 45° C. and at 55° C., as compared to control samples or systems (without test compound) incubated similarly. Any selection of at least one temperature for incubation can be made to perform the screening method, wherein said at least 1 temperature is within a range of about 35° C. to about 65° C. Preferably, at least 2 temperatures or at least 3 temperatures are selected for incubation of said system. In a preferred embodiment, said temperature will be increased over time as compared to the temperature for optimal activity or processivity of the gamma-secretase complex, in a certain incubation period. The temperature(s) of incubation may be applied during a period of incubation and may follow a number of increasing temperature values within said range. The range may be defined in some embodiments from about 35° C. to about 65° C., or from about 37° C. to about 60° C., or from about 37° C. to about 55° C., or from about 40° C. to about 65° C., or from about 40° C. to about 60° C., or from about 40° C. to about 55° C., or from about 40° C. to about 50° C., or from about 40° C. to about 50° C., or from about 45° C. to about 65° C., or from about 45° C. to about 60° C., or from about 45° C. to about 55° C., or from about 45° C. to about 50° C.

In another embodiment, said gamma-secretase complex-destabilizing conditions are induced by addition or presence of a detergent in the system for its incubation in step b). The presence of a detergent in said system destabilizes the gamma-secretase complex by denaturing the membranous compounds present together with the gamma-secretase complex, or by denaturing the protein subunits of the gamma-secretase complex, resulting in a lower processivity of the complex and a release of longer Aβ peptides. The method of the invention aims to produce a compound that stabilizes the gamma-secretase complex in those conditions. Non-limiting examples of detergents that can be added in said system are known by a skilled person and exemplified in the working examples, such as CHAPSO, SDS, Triton X, NP-40, Tween 20, Octyl glucoside, among others.

The invention relates to a method for producing a gamma-secretase stabilizing compound comprising the steps of a) providing a system comprising a gamma-secretase complex, and a peptide APP/Aβ as substrate or a homologue with 95% amino acid identity thereof, or a fragment thereof, followed by b) administering a test compound to said system, and incubating said system in gamma-secretase complex-destabilizing conditions, and c) quantification of the Aβ peptides produced in said system, wherein, under the same test conditions as compared to the same system without the test compound, an increase in the ratio of $A\beta_{38}/A\beta_{42}$ or of $A\beta_{40}/A\beta_{43}$ or of $A\beta_{40}/A\beta_{43}$ or of $(A\beta_{38}+A\beta_{40})/(A\beta_{42}+A\beta_{43})$ peptides identifies said test compound as a gamma-secretase stabilizing compound. "Quantification" of the Aβ peptides produced in said system means that several types and lengths of Aβ peptides are detected or measured using a suitable method for said purpose, known by the person skilled in the art. Following the Aβ peptide quantification, the final ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ can be easily calculated. In one embodiment, said quantification of Aβ peptides comprises immune-based detection, while alternative embodiments relate to a method wherein said quantification of Aβ peptides comprises mass spectrometry. Finally, in another embodiment, a method is provided wherein said quantification of Aβ peptides comprises immune- and MS-based detection. However, as previously stated, a person skilled in the art will also be in the position to apply even further alternative method for quantification of the Aβ peptides, such as for example but not limited to detection of a label added to the substrate, fluorescent detection, quantification of isotope-labelled peptides, or detection via specific tags linked to the peptides.

Detection and quantification is of said produced Aβ peptides in said system is in one embodiment obtained via "immune-based assays" or "immune-based detection" or "immune-based quantification", used interchangeably herein, which refer to the most broadly used bio-detection technologies that are based on the use of antibodies, and are well known in the art. Antibodies are highly suited for detecting small quantities of specific peptides or proteins in the presence of a mixture of peptides or proteins. Said "immune-based detection" refers to a biochemical binding assay involving binding between antibodies and antigen, which measures the presence or concentration of a substance in a sample, such as a biological sample, or an in vitro sample, using the reaction of an antibody to its cognate antigen, for example the specific binding of an antibody to a specific Aβ peptide. Both the presence of the antigen or the amount of the antigen present can be measured. Examples of immunoassays are enzyme linked immunosorbent assays (ELISAs), enzyme linked immunospot assay (ELISPOT), immunobead capture assays, Western blotting, gel-shift assays, protein arrays, multiplexed bead arrays, magnetic capture, fluorescence resonance energy transfer (FRET), a sandwich assay, a competitive assay, an immunoassay using a biosensor, an immunoprecipitation assay etc.

The "capture agent" can be an antibody or fragment thereof that specifically binds Aβ, such as, for example, an antibody or fragment thereof that specifically binds to an epitope located in the forty amino acid residues of Aβ. Some of such antibodies or fragments thereof specifically bind to an epitope located in the first 23 amino acid residues of Aβ. Antibodies are currently available to detect and distinguish each type of resulting Aβ peptide relevant for determination of said ratio: $A\beta_{38}$, $A\beta_{40}$, $A\beta_{42}$, $A\beta_{43}$, can be specifically detected and quantified, for instance via ELISA applying specific antibodies. Some antibodies or fragments thereof specifically bind to an epitope of a fragment generated from cleavage by gamma-secretase at a gamma-secretase substrate, such as, for example, an antibody or fragment thereof that specifically binds to an epitope of an AICD peptide generated from a gamma-secretase substrate. Some of these agents are commercially available, and some such agents can be generated using standard immunogenic techniques (e.g., hybridoma, anti-sera, polyclonal antibody generation). Said antibodies are also applied for detection and quantification for instance by immunoblotting. Furthermore, immunological binding assays frequently utilize a labelling agent that will signal the existence of the bound complex formed by the capture agent and antigen. The labelling agent can be one of the molecules comprising the bound complex; i.e. it can be labelled specific binding agent or a labelled anti-specific binding agent antibody. Alternatively, the labelling agent can be a third molecule, commonly another antibody, which binds to the bound complex (i.e. a secondary antibody). The labelling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labelled streptavidin. Other proteins capable of specifically binding immunoglobulin constant regions, such as protein A or protein G may also be used as the labelling agent. Assays that demonstrate inhibition of either site specific or substrate specific gamma-secretase-mediated cleavage can utilize any of the known forms of gamma-secretase substrates, including the large number of APP forms, such as the non-limiting examples of the 695 amino acid "normal" isotype described by Kang et al., 1987, Nature 325:733-6, the 770 amino acid isotype described by Kitaguchi et al., 1981, Nature 331:530-532, and variants such as the Swedish Mutation (KM670-1 NL) (APPswe), the London Mutation (V7176F), and others. See, for example, U.S. Pat. No. 5,766,846 and also Hardy, 1992, Nature Genet. 1:233-234, for a review of known variant mutations.

The term detectable label or tag, as used herein, refers to detectable labels or tags allowing the detection and/or quantification of the isolated peptides described herein, and is meant to include any labels/tags known in the art for these purposes. Particularly preferred, but not limiting, are affinity tags, such as chitin binding protein (CBP), maltose binding protein (MBP), glutathione-S-transferase (GST), poly(His) (e.g., 6x His or His6), Strep-tag®, Strep-tag II® and Twin-Strep-tag®; solubilizing tags, such as thioredoxin (TRX), poly(NANP) and SUMO; chromatography tags, such as a FLAG-tag; epitope tags, such as V5-tag, myc-tag and HA-tag; fluorescent labels or tags (i.e., fluorochromes/-phores), such as fluorescent proteins (e.g., GFP, YFP, RFP etc.) and fluorescent dyes (e.g., FITC, TRITC, coumarin and cyanine); luminescent labels or tags, such as luciferase; and (other) enzymatic labels (e.g., peroxidase, alkaline phosphatase, beta-galactosidase, urease or glucose oxidase). Also included are combinations of any of the foregoing labels or tags.

Detection and quantification is of said produced Aβ peptides in said system is in another embodiment obtained via "mass-spectrometry" or "MS-based detection" or "mass-spectrometry-based quantification", used interchangeably herein, which refer to detection/quantification methods specifically defining the desired Aβ peptides, such as $A\beta_{38}$, $A\beta_{40}$, $A\beta_{42}$, $A\beta_{43}$. Examples of such MS-based quantification methods are provided herein (see Examples), but also derived from Takama et al. (2009), and from Okochi et al. (2013), the latter for instance applying $A\beta_{45}$ and $A\beta_{46}$ as substrates for gamma-secretase to follow the resulting cleavage products by MS. In another embodiment, the detection and quantification of said produced Aβ peptides in said system comprises both, immune-based and MS-based techniques.

In another embodiment, the method for producing a gamma-secretase stabilizing compound comprises the steps of: providing a system comprising a gamma-secretase complex, and a substrate-like interactor thereof, b) administering a test compound to said system, and incubating said system in gamma-secretase complex-destabilizing conditions, and c) quantification of the binding interaction between said gamma-secretase complex and said substrate-like interactor in said system, wherein, under the same test conditions as compared to the same system without the test compound, an increase in the binding affinity identifies said test compound as a gamma-secretase stabilizing compound.

In a specific embodiment, said gamma-secretase complex-destabilizing conditions are induced by incubating said system in step b) at a temperature in the range of about 35° C. to about 65° C., or more specifically in a range of about 37° C. to about 55° C. In another specific embodiment, said gamma-secretase complex-destabilizing conditions are induced by the presence of a detergent in said system of in step b) of said method.

The term "a substrate-like interactor" herein means a protein or peptide molecule with at least 70% amino acid identity or a homologue of the natural substrates (for examples of natural substrates: see above), or any fragment of such a homologue of a natural substrate, which is able to bind to the substrate-docking site of the catalytic subunit presinilin. A substrate-like interactor is in some embodiments an inhibitor, or an antagonist. Upon providing a system with a gamma-secretase complex and said substrate-like interactor, the binding affinity or interaction between said proteins can be quantified in several ways, using for instance but not limited to, the detection and quantification methodologies provided above, or specifically demonstrating binding properties, such as Surface plasmon resonance, FRET, or Biolayer Interferometry, for instance. The substrate-like interactor can be a labelled or conjugated molecule, for which a person skilled in the art is aware of quantification and detection methods. A non-limiting example for detecting substrate-like interactor binding is provided in Kornilova et al. (2005). Taken into account that said method of the presented invention requires incubation conditions that are gamma-secretase complex-destabilizing conditions, for instance, by incubation at a distinct temperature range, the quantification method for testing whether an increase in binding interaction is present, should allow to be analysed in those gamma-secretase complex-destabilizing conditions, such as in particular higher temperatures. With "Increase in binding affinity" is referred to a change compared to the control in the absence of the compound, preferably, but not by way of limitation, at least of about 5%, at least of about 10%, at least of about 15%, at least of about 20%, at least of about 25%, at least of about 30%, at least of about 35%, at least of about 40%, at least of about 45%, at least of about 50%, at least of about 60%, at least of about 70%, at least of about 80%, or at least of about >90%.

In conclusion, the current invention provides substantial insights into the structural and kinetic mechanisms underlying γ-secretase processivity and support a unifying model for AD causative mutations that places generation of longer Aβ peptides central to AD pathogenesis. Furthermore, the data provide a novel conceptual frame to investigate γ-secretase (dys)function in sporadic AD, as the demonstrated fragility of γ-secretase processivity suggests that mechanisms similar to those underlying FAD may increase the risk of sporadic AD in a subgroup of patients (Szaruga et al., 2015). Finally, these insights guide here to novel efforts to develop safe therapies that target γ-secretase, i.e. the generation of γ-secretase (E-S) stabilizing compounds (GSSC) for the prevention and treatment of AD.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1. Progressive Destabilization of Wild Type γ-secretase-APP Interactions Leads to FAD-Like AR Profiles γ-Secretase sequentially cuts APP to generate Aβ peptides of different length ($A\beta_n$) (Takami et al., 2009).

During this process different enzyme-substrate (E-S) complexes are generated (FIG. 1A). To investigate the relative stabilities of the consecutive E-S complexes, we performed in vitro γ-secretase activity assays across a temperature gradient (from 37° C. to 65° C.), using purified PSEN1/Aph1A γ-secretase and APP$_{C99}$-3XFLAG substrate. Increments in temperature from 37 to 55.1° C. had a modest effect on the initial endopeptidase ε-cleavage (100±15%) (FIG. 1B), but progressively decreased enzyme processivity (the number of γ-cleavages per APP$_{C99}$ molecule), as indicated by the increase in production of long Aβ peptides (FIG. 1C). Specifically, quantitative analyses of substrates (Aβ$_{42}$ and Aβ$_{43}$) and products (Aβ$_{38}$ and Aβ$_{40}$) of the fourth γ-secretase catalytic cycle demonstrates the progressive drop in enzyme processivity (FIG. 1D) and provides an estimate of their "optimum temperature" of production, as well as, the temperature at which production drops to 50% of the initial 37° C. levels (Tm) (FIG. 1E, dotted line). The optimum temperatures for Aβ$_{38}$ (95% CI=31.9 to 36.9° C.), Aβ$_{40}$ (95% CI=38.3 to 40.7° C.), Aβ$_{42}$ (95% CI=43.9 to 46.4° C.) and Aβ$_{43}$ (95% CI=47.8 to 49.6° C.) directly correlate with the length/hydrophobicity of the corresponding peptide, and the same conclusion can be derived from the Tm values (Table 1 for Tm±95% CI). Our data reveal that the E-S complex stability correlates with the substrate length, implying that sequential γ-secretase cleavage on APP progressively decreases the complex stability and increases the probability of E-S dissociation and Aβ release.

Importantly, γ-secretase ε-cleavage of APP$_{C99}$ and Notch, an unrelated alternative substrate (FIG. 1F) implicated in cell-fate determination during development and adult tissue homeostasis (De Strooper et al., 1999), had a similar temperature dependence (FIG. 1G vs. FIG. 1B; 95% CI: 57.4° C.-59.2° C. vs. 60.0° C.-62.4° C., respectively) suggesting that the stabilities of the corresponding E-S complexes are sequence-independent.

Of high relevance, the relative higher stability of the endo-proteolytic cleavage (vs. the γ-cleavages) implies that the associated physiologically relevant signaling cascades, mediated by ε-cleaved intracellular protein domains, would be less susceptible to AD causing mutations or environmental factors destabilizing γ-secretase. Thus, generation of amyloidogenic peptides from APP thermodynamically precedes the general inactivation of the protease upon destabilization of PSEN/γ-secretase.

TABLE 1

Interpolated Tm values and 95% CI intervals derived from experiments presented in FIGS. 3C-D, 4A-B for the ε-activity (right panel) and the γ-cleavages (carboxypeptidase-like activity, left panel) were determined by nonlinear curve fitting (Y = Amplitude * Exp (−0.5*((X − Mean)/SD)$^2$) using GraphPad Prism 7.01 software.

| Endopeptidase Activity | | |
| --- | --- | --- |
| | Tm (° C.) | 95% CI |
| AICD-3XFLAG production PSEN1 | | |
| WT | 61.1 | 60.0 62.4 |
| E280A | 56.6 | 55.2 58.1 |
| M139V | 54.2 | 53.4 55.1 |
| G384A | 48.9 | 47.9 49.9 |
| R278I | 52.4 | 51.4 53.3 |
| Y115H | 53.4 | 52.6 54.3 |
| L166P | 48.5 | 47.8 49.3 |
| L435F | 48.6 | 47.5 49.7 |

TABLE 1-continued

Interpolated Tm values and 95% CI intervals derived from experiments presented in FIGS. 3C-D, 4A-B for the ε-activity (right panel) and the γ-cleavages (carboxypeptidase-like activity, left panel) were determined by nonlinear curve fitting (Y = Amplitude * Exp (−0.5*((X − Mean)/SD)$^2$) using GraphPad Prism 7.01 software.

| APP | | |
| --- | --- | --- |
| WT | 61.1 | 60.0 62.4 |
| T43I | 59.8 | 58.3 61.5 |
| I45F | 56.4 | 55.2 57.6 |
| V46F | 55.4 | 54.3 56.5 |
| V46I | 58.0 | 56.8 59.4 |
| PSEN1-APP | | |
| E280A - WT | 56.6 | 55.2 58.1 |
| E280A - V46F | 50.3 | 49.3 51.4 |
| E280A - I45F | 49.7 | 48.3 51.0 |

| Carboxypeptidase-like Activity | | |
| --- | --- | --- |
| | Tm (° C.) | 95% CI |
| Aβ38 generation | | |
| WT | 47.1 | 46.2 48.0 |
| E280A | 45.0 | 43.9 46.2 |
| M139V | 44.0 | 43.0 44.9 |
| G384A | 44.2 | 42.7 45.6 |
| Y115H | 44.3 | 43.7 44.8 |
| L166P | 43.9 | 42.5 45.2 |
| Aβ40 generation | | |
| WT | 50.4 | 49.8 51.0 |
| E280A | 45.4 | 43.8 47.2 |
| M139V | 46.2 | 45.4 47.2 |
| G384A | 44.2 | 42.6 45.7 |
| Y115H | 45.6 | 45.0 46.3 |
| L166P | 41.9 | |
| Aβ42 generation | | |
| WT | 54.7 | 53.5 56.1 |
| E280A | 48.8 | 47.4 50.5 |
| M139V | 47.9 | 46.9 49.1 |
| G384A | 45.3 | 44.0 47.0 |
| Y115H | 47.0 | 45.3 49.2 |
| L166P | 41.0 | 40.1 41.7 |

Example 2. Membrane Components Stabilize γ-Secretase-Substrate Interactions

Figure 2:
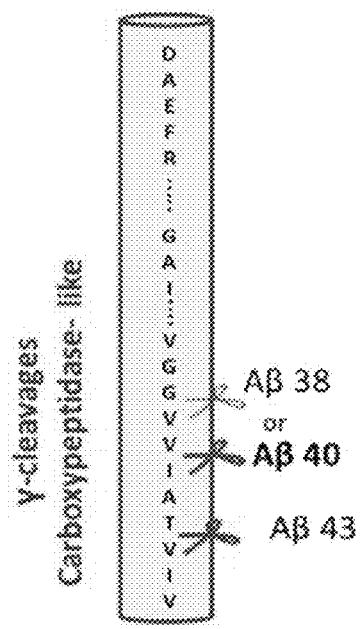
FIG. 2. Kinetic analyses of the sequential processing of A$\beta_{46}$ and A$\beta_{45}$ by wild type $\gamma$-secretase A, D) Schematic processing of A$\beta_{46}$ and A$\beta_{45}$ by $\gamma$-secretase, respectively. B-G) Thermo-activity assays using purified $\gamma$-secretase and synthetic A$\beta_{46}$ or A$\beta_{45}$ as substrates. B) A$\beta_{43}$ product levels at 37° and 51° C. was fit with a Michaelis-Menten model (fit±95% CI), (mean±SEM, n=4). Notice that part of the de novo A$\beta_{43}$ generated in the reactions is further processed to A$\beta_{40}$ or A$\beta_{38}$; thus total A$\beta_{43}$ generated is estimated here as A$\beta_{43}$+A$\beta_{40}$+A$\beta_{38}$. C) Subsequent conversion of A$\beta_{43}$ into shorter A$\beta_{40}$ (or A$\beta_{38}$, not shown) at 37° C. or 51° C.; (mean±SEM, n=4). E) Sequential processing of A$\beta_{45}$ into A$\beta_{42}$ fit with a Michaelis- Menten model (fit±95% CI) and F) subsequent cut to $A\beta_{38}$ at the indicated temperatures (mean±SEM, n=3). Notice that part of the de novo $A\beta_{42}$ generated in the reactions is further processed to $A\beta_{38}$; thus total $A\beta_{42}$ is calculated as $A\beta_{42}$+$A\beta_{38}$. G) $A\beta_{40}/A\beta_{43}$ and $A\beta_{38}/A\beta_{42}$ ratios indicate that $A\beta_{43}$ is less efficiently processed than $A\beta_{42}$ at 37° C.; while both cleavages are strongly impaired at 51° C. Graph includes all data points shown in panels C and F (mean±SEM, t-test, $P_{value}$<0.0001). H) The sequential γ-secretase cuts on APP progressively decrease the E-S complex stability and increase the probability of dissociation. E-S complexes with $A\beta_{\leq 46}$ substrates (in red) are the most susceptible to (dys) regulation.
Figure 2:
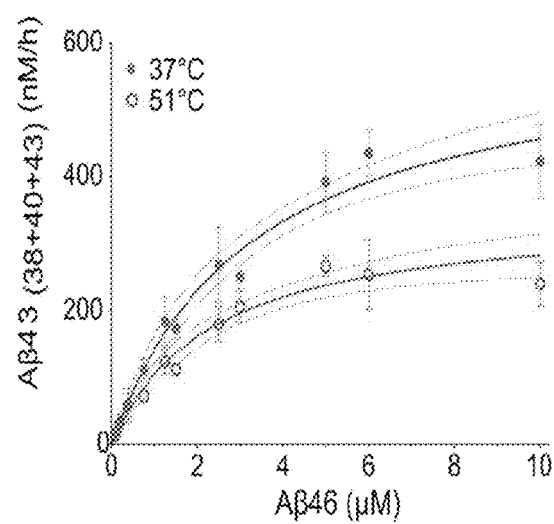
Figure 2:
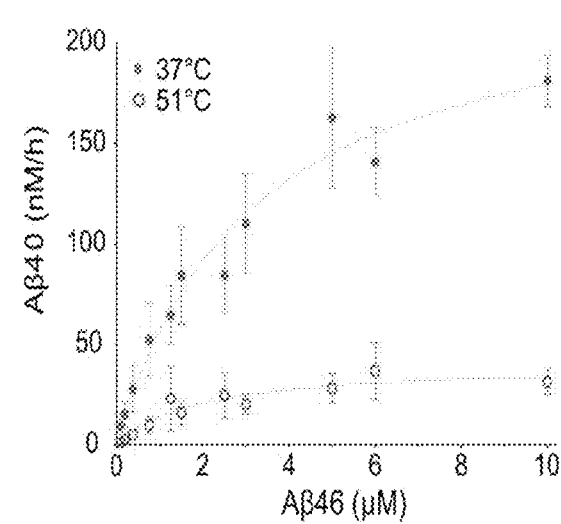
Figure 2:
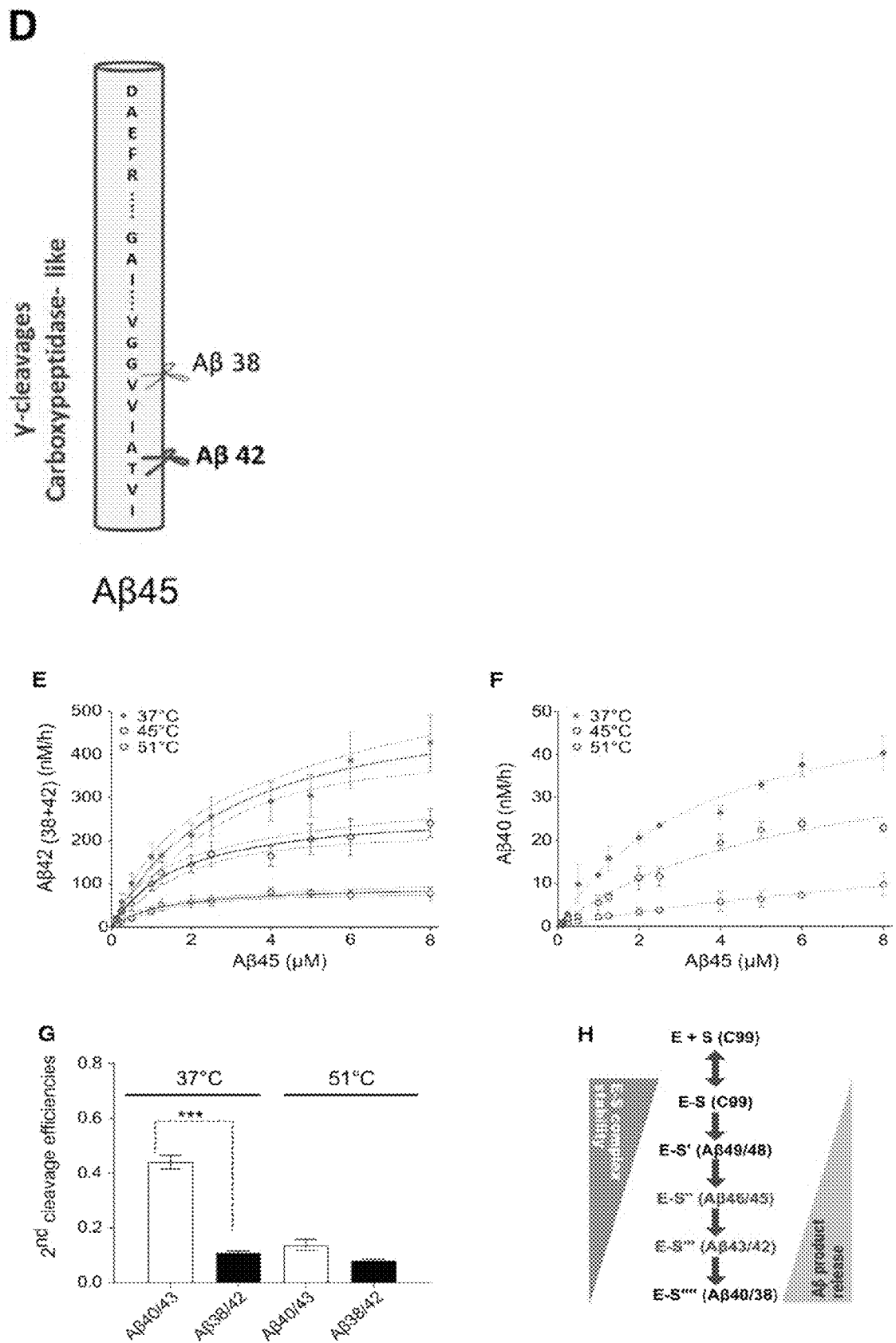

The evaluation of γ-secretase kinetics in CHAPSO solubilized conditions is a common practice in the field. However, compared to cell-based assays (Sato et al., 2003), these conditions promote the generation of long Aβ$_{≥42}$ peptides. Based on the experimental evidence above, we hypothesized that detergent extraction, similar to increasing temperature, might destabilize γ-secretase and therefore impair processivity. Hence, we assessed γ-secretase function in CHAPSO resistant membranes (DRMs), an alternative and well validated cell-free system for the study of γ-secretase activity (Kakuda et al., 2012; Matsumura et al., 2014; Szaruga et al., 2015; Wahrle et al., 2002) that yields similar Aβ ratios as cell-based assays (FIG. 8B-C). We prepared DRMs from four post-mortem human brain samples of control subjects. Thermal analysis of ε-endopeptidase activity evaluated by de novo AICD generation, revealed no significant changes over the 37-65° C. temperature interval (FIG. 1H), demonstrating the stabilizing effect of DRMs on γ-secretase activity (compare FIG. 1H vs. 1B). In contrast, a mild increment in temperature significantly affected γ-secretase processivity (73.2%±10.0 at 40° C.; mean of means±SD) (FIG. 1I) and remarkably, further temperature increments reduced enzyme processivity to the levels seen in FAD patient brain samples (59.4%±2.3 at 45° C. and 20.3%±5 at 55° C.; mean of means±SD of control brain DRMs vs. 44.4%±13.6 at 37° C. mean of means±SD of 22 FAD brain DRMs; data for FAD taken from FIG. 2 in (Szaruga et al., 2015)). These studies demonstrate that the membrane environment shapes Aβ peptide profile by stabilizing the most labile γ-secretase-Aβ$_n$ complexes and that thermal destabilisation of wild type γ-secretase leads to Aβ profiles similar as those seen in FAD.

Example 3. Aβ$_n$ Substrate Length is a Determinant for E-S Complex Stabilities

Figure 3:
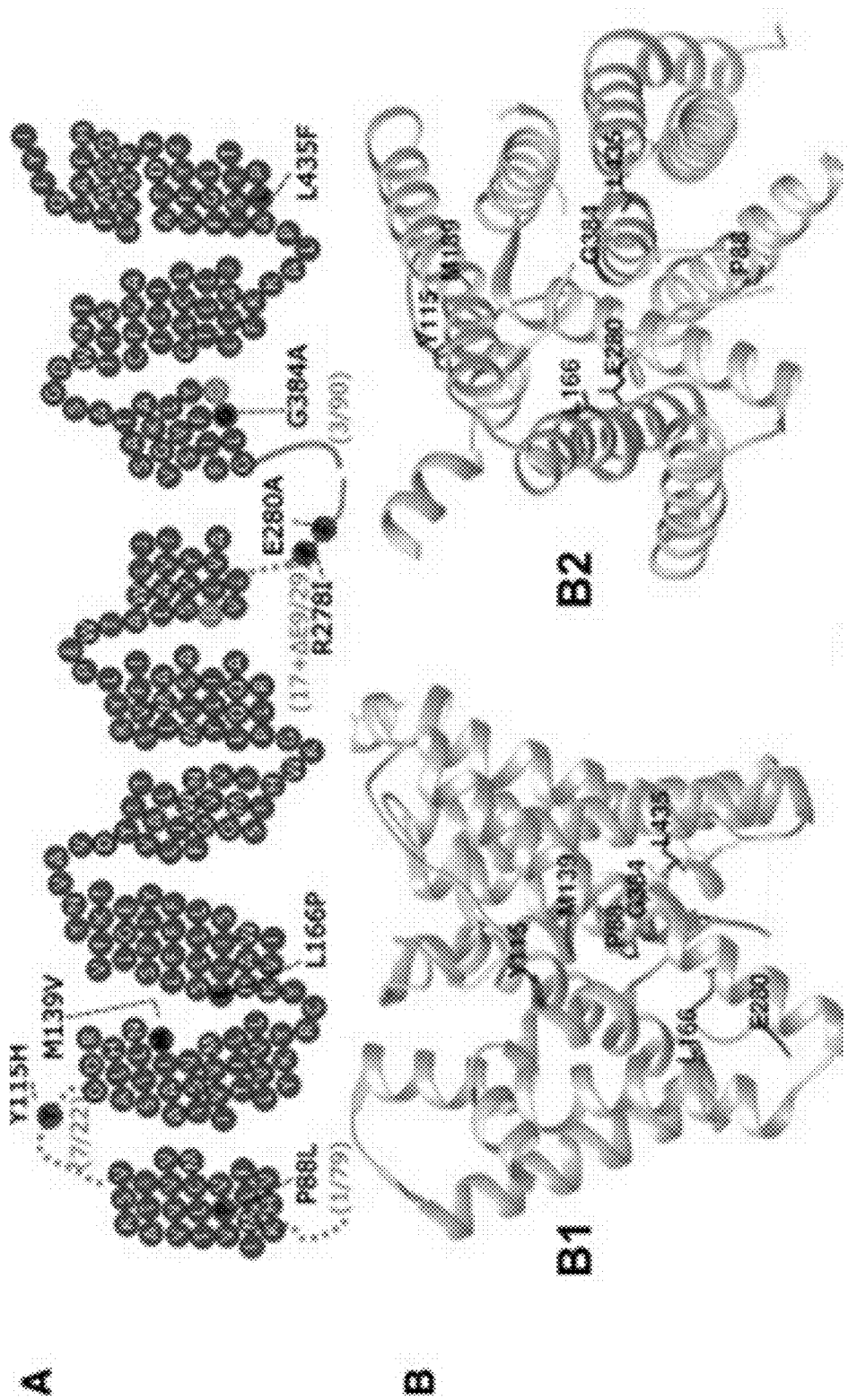
FIG. 3. AD-linked PSEN1 mutations impair the stability of γ-secretase-substrate complex A) Scattered distribution of PSEN residues mutated (red) in FAD. B) 3-D Location of the selected PSEN1 mutations (red), except for the R278 which is not resolved in the 3D structure. Catalytic Asp residues shown in yellow. B1) lateral and B2) bottom views of PSEN1 structure (brown) with a co-purifying peptide (grey) (PDB: 5fn2). C-D) Thermo-activity assays using purified wild type or mutant γ-secretase complexes and C99-3xFLAG substrate. Incubation was for 20 min at the indicated temperatures, except for the severe P88L mutant protease which activity was measured after 1 h and its concentrations was 10× higher. C) Representative immuno-blots showing AICD-3XFLAG levels generated by the different protease complexes (top panel). Lower panel shows Gaussian fittings on AICD-3XFLAG product levels; (mean±SEM, n=4). D) Gaussian fittings on ELISA quantified $A\beta_{38}$, $A\beta_{40}$ and $A\beta_{42}$ peptides produced by wild type or mutant γ-secretase complexes at the indicated temperatures (top, middle and lower panels, respectively); (mean±SEM, n=4). The relative shifts in apparent Tm's (dotted line) demonstrate the destabilizing effects of AD causative mutations. E-F) Apparent Tm±95% CI for AICD generation and $A\beta_{42}$ production by mutant enzymes vs. the corresponding age of onset of AD in patients (AICD: y=0.3678*x+38.66; ±95% CI for 5 out of 8 mutants and $A\beta_{42}$: y=0.3509*x+32.48; ±95% CI). Notice that P88L, L435F and R2781 are the more severe 'loss' of function mutations, and apparently show a delayed age of onset (y=0.8843*x+7.971, dotted line).
Figure 3:
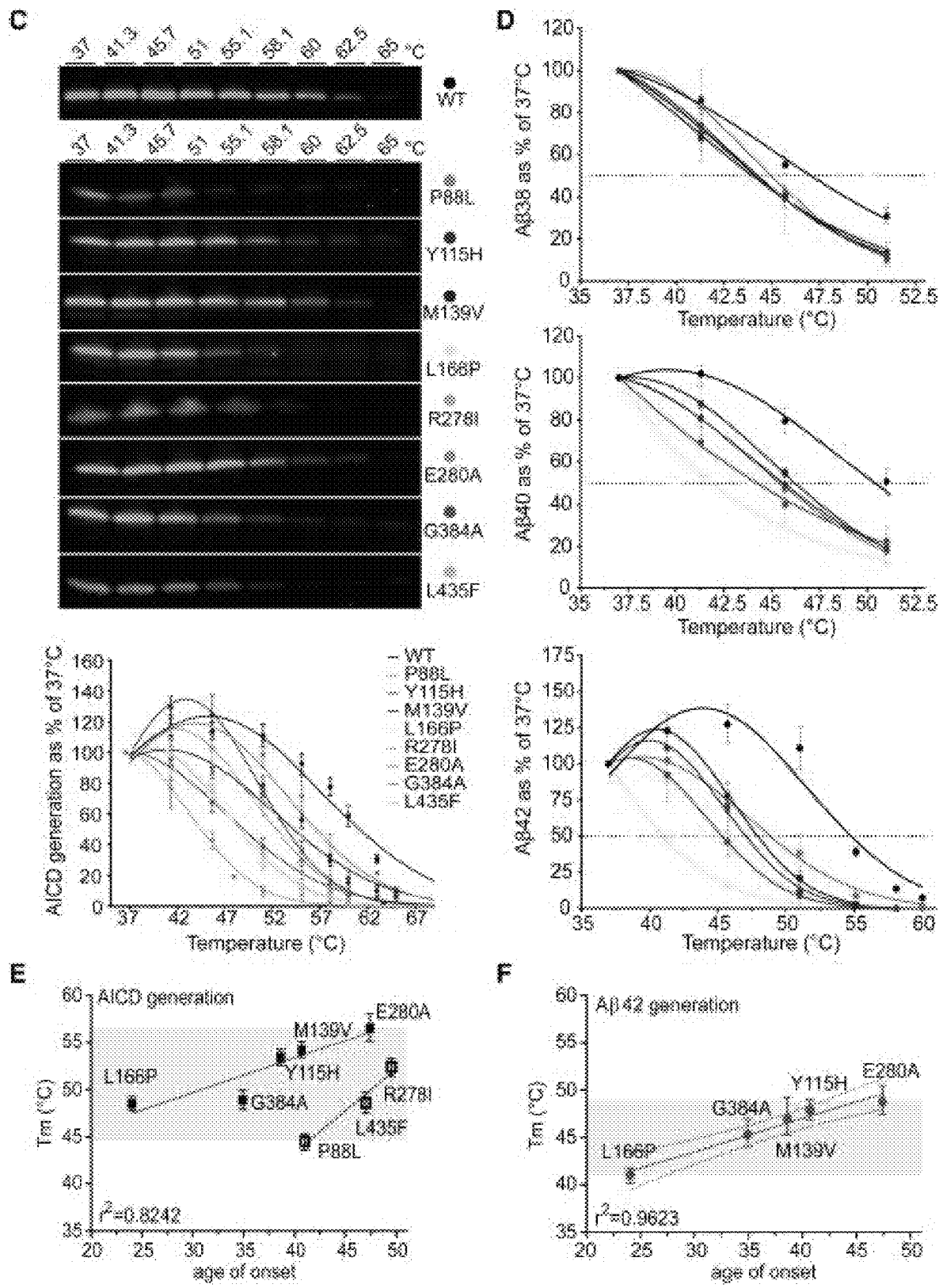

Given that E-S complexes containing relatively long Aβ$_n$ peptides (n=45, 43 and 42) are the most labile and therefore susceptible to dysregulation, we investigated the conversion of synthetic Aβ$_{46}$ to Aβ$_{43}$ (FIGS. 2A and 2B) and Aβ$_{46}$ to Aβ$_{42}$ (FIGS. 2D and 2E) by purified wild type enzyme at various temperatures. The two peptide substrates differ only by one amino acid but display distinct thermal susceptibilities (FIG. 2B vs E), indicating that the relative stability of the E-Aβ$_{46}$ complex is higher. For instance, the γ-secretase-Aβ$_{46}$ complex is two times more stable than the γ-secretase-Aβ$_{45}$ complex at 51° C. (kinetic parameters summarized in Table 2). The importance of substrate length for E-S stability is further illustrated by the observation that generation of Aβ$_{43}$ from Aβ$_{46}$ occurs with similar efficiencies at 37° C. and 51° C. (FIG. 2B and Table 2), while its further conversion (in the same reaction mix) to A1340 drastically decreases (~82%) at 51° C. (FIG. 2C). Similarly, the Aβ$_{40}$/Aβ$_{43}$ and Aβ$_{38}$/Aβ$_{42}$ ratios (FIG. 2G), which provide estimates for the efficiencies of the corresponding cleavages, indicate that γ-secretase cuts Aβ$_{43}$ more efficiently than Aβ$_{42}$ already at 37° C. Our data confirm that E-S complex stability directly correlates with Aβ length; and the decreasing stabilities of E-S complexes with peptides <Aβ$_{46}$ strongly point to a critical Aβ substrate length for efficient γ-cleavage processing (FIG. 3H). Remarkably, the effect of temperature on the catalytic efficiencies are explained by decreased proteolytic rates (Vmax) (Table 2) rather than by changes in affinity (Km) as will be discussed below.

TABLE 2

Kinetic parameters for wild type human γ-secretase (PSEN1/APH1a), using synthetic Aβ$_{46}$ or Aβ$_{45}$ as substrates. Kinetic values derived from the data presented in the FIGS. 2B and 2E determined by nonlinear curve fitting (Y = Vmax * X/(Km + X)) using GraphPad Prism 7.01 software.

| Aβ46 → Aβ43 | Vmax | | Km | | Efficiency |
|---|---|---|---|---|---|
| | nM/h | 95% CI | µM | 95% CI | % |
| 37° C. | 606.3 | 504.2 to 752.5 | 3.3 | 2.1 to 5.2 | 100.0 |
| 51° C. | 348.8 | 284.3 to 442.6 | 2.3 | 1.4 to 4 | 80.9 |
| 37° C. | 545.2 | 420.3 to 788.3 | 2.9 | 1.5 to 6.2 | 100.0 |
| 45° C. | 274.3 | 222.5 to 357.4 | 1.7 | 0.9 to 3.4 | 83.6 |
| 51° C. | 97.45 | 80.3 to 122.3 | 1.4 | 0.73 to 2.6 | 44.6 |

Example 4. AD-Linked PSEN Mutations Destabilize γ-Secretasesubstrate Complexes

We next investigated the effect(s) of AD-linked PSEN mutations on the stability of the γ-secretase cleavages. We selected eight pathogenic PSEN1 mutations (P88L, Y115H, M139V, L166P, R278I, E280A, G384A and L435F) that impair the ε-endo and γ-carboxypeptidase-like activities to different extents (Chávez-Gutiérrez et al., 2012; Saito et al., 2011; Veugelen et al., 2016), differ in age of onset and location throughout PSEN1 (FIG. 3A, 3B and Table 3). The R278I and L435F mutations additionally affect activation of the γ-secretase pro-enzyme (PSEN auto-proteolysis) and drastically reduce levels of the active γ-secretase in cells (Saito et al., 2011; Veugelen et al., 2016). Thermo-activity assays using purified wild type or mutant γ-secretase complexes and the APP$_{C99}$-3XFLAG substrate reveal that PSEN mutations consistently shift Tm values for AICD-3XFLAG (FIG. 3C), Aβ$_{38}$, Aβ$_{40}$ and Aβ$_{42}$ production (FIG. 3D; upper, middle and lower panels, respectively). Thus, clinical mutations consistently destabilize, to different extents, the productive interaction with APP$_{C99}$ and de novo Aβ$_n$ substrates, relative to the wild type enzyme (Table 1). As previously reported, the P88L, R278I and L435F γ-secretase complexes drastically reduce the endopeptidase activity and produce mostly Aβ$_{43}$ and longer peptides at 37° C. (Ohki et al., 2014; Saito et al., 2011; Veugelen et al., 2016). The activities of these mutants rapidly decay with increasing temperature (FIG. 3C and FIG. 9), indicating severe destabilisation of the intermediary and initial E-S complexes. This likely explains their inefficient endo- and carboxypeptidase activities at normal body temperature. The other PSEN mutations display significant, but relatively mild destabilizing effect on Aβ$_{38}$ production (FIG. 3D; upper panel, see also the corresponding Tm values in Table 1). Given that Aβ$_{42}$ is the main precursor of Aβ$_{38}$, the relatively fast decay Aβ$_{38}$ production reflects the high probability of Aβ$_{42}$ release, explaining why it is the major product on the Aβ$_{48}$→Aβ$_{38}$ production line. The destabilizing effects induced by pathogenic mutations becomes clearer when analyzing Aβ$_{40}$ and Aβ$_{42}$ generation, which reflects the processing of Aβ$_{43}$ and Aβ$_{45}$ substrates, respectively (FIG. 3D; middle and low panels). The Tm values (Table 1) determined for pathogenic PSEN variants are consistently lower than the corresponding wild type values. These findings indicate that the destabilizing effects induced by PSEN mutations result in increased E-Aβ$_n$ complex dissociation rates and hence enhance release of longer Aβ peptides. The clinical relevance of this concept is supported by the remarkable correlation between the mutant-induced destabilizing effect (Tm's) for ε-endopeptidase (FIG. 3E) or γ-carboxypeptidase activity (FIG. 3F), and the age of onset for 5 out of 8 PSEN mutations. Intriguingly, our data suggest that patients with the P88L, R278I and L435F mutations, which impact γ-secretase to the most severe extent, have a "delayed" age of onset despite the drastic effect on γ-secretase processivity (generation of long Aβ$_{>43}$). We propose that the extremely low global activity of the mutated allele counteracts the deleterious effects that may be associated with the enhanced production of long Aβ peptides, therefore lowering the overall pathogenic effect and hence resulting in a later age at onset than would otherwise be seen.

Example 5. AD-Linked APP Mutations Prime "γ-Secretase-AR Complexes" for Dissociation Given that our studies place the E-S complex stabilities central to FAD pathogenesis, we investigated if pathogenic substitutions in APP affect these key assemblies. The T43I-, I45F-, V46F- and V46I-APP mutations (Table 3) were chosen for analysis in thermo-activity assays with purified wild type γ-secretase. At the endopeptidase level, three mutations exerted mild destabilizing effects while T43I did not differentiate from the wild type (FIG. 4A and Table 1). We then evaluated if the destabilizing effects of clinical mutations in PSEN and APP were additive. For that we selected the E280A-PSEN mutation, which has a mild destabilizing effect (FIG. 3C). Endo-proteolytic processing of the V46F and I45F-APP substrates by the mutant E280A-PSEN1/γ-secretase over a temperature gradient demonstrated additive effects (FIG. 4B and Table 1), strongly supporting converging detrimental effects of APP and PSEN clinical mutations.

Next, we studied in depth the processing of mutant APP substrates in a membrane-like environment (DRM). DRMs were prepared from insect cells expressing wild type γ-secretase (Acx et al., 2014). γ-Secretase products were directly detected and relatively quantified by MALDI-TOF and MALDI-FTICR mass spectrometry without any enrichment steps (FIG. 10A). Employing this method, we verified the production of $A\beta_{45}$ (FIG. 10C), the stabilizing effect of the membrane-like environment and the relatively weak effect of pathogenic mutations in APP on AICD generation (FIG. 10I vs. FIG. 16/4A). We also confirmed the previously observed shift in the position of the ε-cleavage that favours the $A\beta_{48} \rightarrow A\beta_{42}$ product line linked to the T43I, V46F and V46I substitutions, but not to the I45F (Bolduc et al., 2016; Chávez-Gutiérrez et al., 2012; Dimitrov et al., 2013) (FIG. 4C). As shown above, E-S complexes containing $A\beta_n$ peptides are more prone to destabilization. Thus, we analysed how these mutations affect the temperature sensitivity of Aβ generation. For the wild type APP substrate, thermo-activity assays show progressive decrements in the generation of $A\beta_{40}$ (major product) and increments in the $A\beta_{43}$ precursor over the 37° C.-65° C. range (FIG. 4D). Similarly, $A\beta_{38}$ levels (minor product) gradually fall. $A\beta_{38}$ is generated from both $A\beta_{42}$ and $A\beta_{43}$ (Matsumura et al., 2014; Okochi et al., 2013), thus its decrement contributes partially to the increases in $A\beta_{43}$ and to the stabilized $A\beta_{42}$ levels up to 58° C. Beyond 58° C., increased release of the precursor $A\beta_{45}$ is seen in urea-based gel electrophoresis (FIG. 4J, 55° C.).

Similar analyses revealed that the T43I substitution increases the thermal susceptibilities observed for the $A\beta_{38}$, $A\beta_{40}$, $A\beta_{42}$ and $A\beta_{43}$ products generated from the wild type substrate (FIG. 4E compare to 4D), indicating a mutant-induced destabilizing effect on E-S complexes with long A13>43 substrates. In support of this, T43I-mutant Aβ profiles show long Aβ products at 37° C. and their levels increase with temperature (FIG. 4J, FIG. 10D). As the T43I mutation drastically shifts the position of the ε-cleavage to favor $A\beta_{48}$ generation (FIG. 4C), we speculate that the longer Aβ products are $A\beta_{45}$ and/or $A\beta_{48}$.

As previously reported, no $A\beta_{40}$ nor $A\beta_{43}$ products are generated from the mutant I45F-APP substrate due to a mutant-induced product-line shift that involves the conversion of $A\beta_{46}$ to $A\beta_{42}$ (Bolduc et al., 2016). Aβ profiles confirmed the presence of $A\beta_{38}$ and $A\beta_{42}$, and showed the presence of a longer Aβ product at 37° C., with $A\beta_{46}$ mobility (FIG. 4J). Increments in temperature induced progressive decrements in $A\beta_{38}$ (FIG. 4F) and increased $A\beta_{42}$ and $A\beta_{46}$ levels over the 37-65° C. interval (FIG. 4J).

Finally, the thermo-activity assays with V46F and V46I APP mutations show enhanced $A\beta_{38}$ and $A\beta_{42}$ decays (FIGS. 4G and 4D, respectively and FIG. 10F) and increasing $A\beta_{43}$ levels at temperatures above 50° C. (FIG. 5D and FIG. 10G), relative to the wild type substrate. Thus, these pathogenic substitutions (in particular the V46F mutant) destabilize the γ-secretase-$A\beta_{43}$ interaction and may also impair mutant E-S complexes containing Aβ peptides longer than 43. We expressed transiently the V46F/I substrates and quantified by ELISA secreted $A\beta_{40}$ and $A\beta_{43}$ peptides. As expected, the $A\beta_{40}/A\beta_{43}$ ratios are strongly reduced confirming the destabilized γ-secretase-$A\beta_{43}$ interaction (FIG. 4I). Analyses of the V46F/I-Aβ product profiles generated in DRM-based reactions in urea based electrophoresis support enhanced $A\beta_{45}$ production from the V46I substrate at 55° C., relative to the wild type reaction (FIG. 4J).

Overall, our data indicate that the T43I, I45F and V46I mutations destabilize the E-S complexes with $A\beta_{48}$, $A\beta_{46}$ and $A\beta_{45}$, respectively, leading to dissociation and release of these long Aβ peptides. Intriguingly, the V46F mutant destabilizes the 'wild type' γ-secretase-$A\beta_{43}$ complex. The V46F substitution drastically shifts the ε-cleavage position to favour the $A\beta_{42}$ product line (FIG. 4C), and nevertheless still generates substantial amounts of $A\beta_{40}$ at 37° C. (FIG. 4J), which suggest that the phenylalanine substitution promotes the alternative cleavage of $A\beta_{48}$ to $A\beta_{43}$ ($A\beta_{40}$ precursor) (Matsumura et al., 2014). However, the additional effects of this mutation on docking/presentation of the substrate to the catalytic site and/or endopeptidase cleavage specificity (different AICD and therefore long Aβ products are generated, FIG. 4C) may contribute to the observed effects. In conclusion, our data demonstrate that APP mutations located around the γ-cleavage sites impact the stability of E-$A\beta_n$ complexes and consequently enhance product dissociation and the release of long amyloidogenic Aβ peptides by a similar mechanism to that proposed for PSEN pathogenic mutations (FIG. 4B).

TABLE 3

Shows the location of the selected FAD-linked mutants and summarizes clinical and kinetic data. Kinetic efficiencies are reported in (Chavez-Gutierrez et al., 2012)[1], (Veugelen et al., 2016)[2] or not determined (ND).

| PSEN1 | Location | Age of Onset | 4th γ-cleavage efficiency (Aβ38/42 as % of WT) | ε-cleavage efficiency (as % of WT) |
|---|---|---|---|---|
| P88L | TM-I | 41* | ND | ND |
| Y115H | HL-I | 38.5 | 10% (1) | 30% |
| M139V | TM-II | 40.7 | 40% (1) | 100% |
| L166P | TM-III | 24 | 30% (1) | 45% |
| R278I | HL-VI | 50 | 15% (2) | 35% |
| E280A | HL-VI | 47.4 | 30% (2) | 60% |
| G384A | TM-VII | 34.9 | 30% (1) | 25% |
| L435F | TM-IX | 47 | ND | ND |

| Aβ (APP) position | Name | Age of Onset | 4th γ-cleavage efficiency (Aβ38/42 as % of WT) | ε-cleavage efficiency (as % of WT) |
|---|---|---|---|---|
| T43I (T714I) | Austrian | 36.3 | 160% (1) | 30% (1) |
| I45F (I716F) | Iberian | 31 | ND | ND |
| V46F (V717F) | Indiana | 41.2 | 100% (1) | 70% (1) |
| V46I (V717I) | London | 52 | 110% (1) | 110% (1) |

Example 6. Exogenous Factors Stabilize or Destabilize γ-Secretase-Substrate Interactions Previous studies have shown that diverse compounds, referred to as γ-secretase inverse modulators, mimic FAD-linked mutations by enhancing $A\beta_{42}$ generation from the wild type enzyme (Kukar et al., 2005). In contrast, γ-secretase modulators (GSMs) (Weggen et al., 2001), including endogenous metabolites (Jung et al., 2015), enhance protease processivity (Chávez-Gutiérrez et al., 2012; Takeo et al., 2014). However, their mechanisms of action remain elusive.

We tested three different GSM chemistries (FIG. 5A) in γ-secretase thermo-activity assays. As expected, the direct γ-secretase modulators GSM A and B and the inverse modulator fenofibrate (GSM C) (Kukar et al., 2005) increased and decreased the conversion of $A\beta_{42}$ to $A\beta_{38}$ at 37° C., respectively (FIG. 5B). More interestingly, the addition of 10 μM direct GSM to wild type enzyme maintained elevated protease processivity ($A\beta_{38}/A\beta_{42}$) over the 37-55° C. interval (FIG. 5B), supporting an effect of stabilization of the γ-secretase-$A\beta_{42}$ interaction. The compound mediated stabilization is observed to a certain extent at the endopeptidase level (AICD production), especially with GSM B (FIG. 5C). Remarkably, fenofibrate leads to important reductions in AICD production at increasing temperatures, which is indicative for a strong destabilizing effect on γ-secretase-APP substrate complexes. Our data provide mechanistic insights into the mode of action of therapeutically relevant compounds. Furthermore, these results highlight the possibility that environmental factors affecting the stability of the most labile E-S complexes (containing short $A\beta_s$) could alter the risk for sporadic AD.

Example 7. Elevation in Body Temperature Modulates γ-Secretase Activity In Vivo

Given the observed high thermal susceptibility of the PSEN/γ-secretase activity (FIG. 1I), we evaluated the effect of elevated temperature in intact cells. For that we incubated HEK293 cells stably overexpressing human APP695$_{KM670/671NL}$ (Swedish mutation) for 1 hour at 37° C. or 42° C. Cell viability was not affected by this short incubation time. ELISA quantification of secreted Aβ showed a significant increase of total Aβ produced, especially of $A\beta_{43}$ (FIGS. 6A and 6B) and a significant reduction in the ($A\beta_{38}+A\beta_{40}$)/($A\beta_{42}+A\beta_{43}$) ratio (products/substrates of the 4$^{th}$ catalytic cycles) at 42° C., relative to 37° C. (FIG. 6C).

Next, we wondered whether increased body temperature could modulate γ-secretase activity in vivo. We thus induced fever in mice carrying humanized Aβ sequence and the AD-linked Swedish (KM670/671 NL) APP mutation (Saito et al., 2014). Treated mice received an injection of 30 μg LPS intraperitoneally and were kept in a warmed cage (~38.5° C.) (Jiang et al., 1999). The treated mice reached a body temperature of 40° C. (±0.5° C.) 25 minutes post-injection which was maintained for max 2 hours (FIG. 11A). Control animals injected with saline solution and kept at room temperature (RT, ~23° C.) had body temperatures around 38° C. Quantification of steady-state Aβ levels in plasma by ELISA revealed increased total Aβ levels (1.88 fold) in treated vs. control mice and relative increments of 1.51, 1.94 and 1.82 fold for $A\beta_{38}$, $A\beta_{40}$ and $A\beta_{42}$, respectively (FIG. 6D). Accordingly, $A\beta_{38}/A\beta_{42}$ ratio is lowered in the treated mice (FIG. 6E). We cannot exclude that other factors, apart from elevated body temperature, might have contributed to the observed changes in Aβ; however, the results obtained in cell culture provide support to the in vivo findings. The fact that elevated body temperature augments γ-secretase activity and impairs the efficiency of the 4$^{th}$ γ-cleavage further supports the idea that exogenous factors may impact γ-secretase-$A\beta_n$ metastable structures and therefore contribute to onset in familial AD or alter the risk for sporadic AD.

8. Discussion of the Examples

The invention relates to the finding that clinical mutations in PSEN and in APP destabilize primarily the intermediary E-S complexes involved in the sequential processing of APP by γ-secretase, leading to enhanced E-S dissociation and thereby release of longer, more amyloidogenic, Aβ peptides. By applying progressive thermal destabilization of the wild type enzyme to evaluate the strength of the different E-S interactions (FIGS. 1A and 1E), surprisingly, increments in temperature were demonstrated to mimic the effects of clinical AD mutations. Our studies revealed a direct correlation between the length of the substrate and E-S complex (thermo)stability, indicating that each γ-secretase cleavage reduces the stability of the subsequent E-S complex and thereby progressively shifts the equilibrium towards dissociation and release of peptides $A\beta_{\leq 42}$. Direct determination of the substrate affinity constants for APP-$C_{99}$ (Km ~400-800 nM (Chávez-Gutiérrez et al., 2012; Funamoto et al., 2013)) and for $A\beta_{46}$ or $A\beta_{45}$ substrates (Km ~3 μM, Table 2) support this concept.

We propose that γ-secretase-APP$_{C99}$ complexes are stabilized by a network of weak bonding interactions along the substrate transmembrane domain (TMD) (global fitting). In this scenario the stabilizing binding energy depends critically on the area of interacting surface, i.e. on the substrate length, while the side chains of the constituting residues are not the main driving force for the formation nor for the stabilities of the E-S complexes. This view is supported by the known relaxed γ-secretase substrate specificity and the similar (sequence independent) thermo-stabilities seen for the ε-cleavage of APP and Notch based substrates (FIG. 2F). However, in sharp contrast, we observed that single amino acid substitutions in APP can exert a profound destabilizing effect on the E-$A\beta_n$ complexes, which translates into altered Aβ profiles. These findings imply that the type of interactions involved in the stabilization of the initial ε-E-S vs. the consecutive γ-E-S complexes are fundamentally different.

While the nature of the E-S interaction remains unknown, the recently elucidated high-resolution structure of γ-secretase in complex with a co-purifying type I transmembrane protein provides interesting insights. As shown in FIG. 7, a short helical structure anchors the putative substrate to PSEN-NTF, while an unstructured stretch of ~5 amino acids extends through a wide channel to reach the catalytic residues (Bai et al., 2015b). In our view, this co-structure could illustrate how an $A\beta_n$, product interacts with PSEN before it engages in the next catalytic cycle, or is released. In the former case, further unwinding of the N-terminal helix must occur in order to fill the S1'-S3' enzyme pockets (Bolduc et al., 2016) during the next transition state (FIG. 7). This will lead to further destabilization of the anchor helix, which weakens the E-S assembly and importantly, give progressively more significance to other interactions (side chain dependent) along the $A\beta_n$, substrate. This model explains why AD-linked substitutions in APP ($A\beta_{42-46}$) destabilize γ-secretase-Aβ but not γ-secretase-APP$_{C99}$ complexes. In fact, the presented data indicate that $A\beta_{45}$ and $A\beta_{46}$ substrates are of a critical length as the following γ-cut drastically reduces the stability of the subsequent γ-secretase-$A\beta_{43/42}$ complexes (FIGS. 3C and 3F). According to the E-Aβ interaction model (FIG. 7), this can best be understood by taking into account the fact that unstructured C-terminal stretches of ~5 amino acids leave N-terminal helical anchors of 13 aa, 12 aa, 10 aa or 9 aa in the $A\beta_{46}$, $A\beta_{45}$, $A\beta_{43}$ or $A\beta_{42}$ peptides, respectively. It appears that an N-terminal helical anchor with at least 3 turns ($A\beta_{46}$) stabilizes E-S interactions and promotes efficient γ-secretase processing.

The pathogenic PSEN1 mutants, irrespective of their nature or position, destabilize E-S complexes (FIGS. 4E-G) and previous work (Chávez-Gutiérrez et al., 2012) analysing the ε-cleavage show that their effects are not explained by lower substrate affinities but rather by reduced catalytic rates (decreased Vmax, see also Table 2). This indicates that thermal destabilization and clinical mutations do not affect directly the formation of 'γ-secretase-Aβ$_n$' complexes but instead affect a subsequent step in catalysis. Upon E-S formation, the complex can either decompose back to free enzyme and substrate or undergo catalysis via a transition state intermediate (E-S* complex), which involves structural rearrangements in both the enzyme and the substrate. In general, a higher affinity for the transition state drives catalysis. In the γ-secretase proteolytic mechanism, the stabilization of the transition state likely involves, as explained, local helix unwinding prior to cleavage and the resultant backbone break must have a destabilizing effect on the remaining helical structure of the subsequent de novo Aβ$_n$ substrates (FIG. 7).

Although our knowledge of intramembrane proteolytic mechanisms remains very limited, insights from the rhomboids also indicate that the substrate (TMD) helical propensity is crucial for the E-S interaction and that proteolysis is driven by kinetic rate, rather than substrate affinity (Dickey et al., 2013; Moin and Urban, 2012). We propose that FAD-linked PSEN mutations, or increased temperature, result in a less efficient stabilization of the E-S*transition state, leading to enhanced product release during E-S* rearrangements. Support for this hypothesis comes from experiments showing that FAD-linked G384A and Delta Exon 9 PSEN mutations decrease the affinity for the transition-state analogue L-685,458 (Svedruzic et al., 2012). A lack of affinity for the transition state may either lead directly to dissociation (E-S*→E+S) or restore the E-S state (E-S←E-S*). In the case of the APP-CTF substrate, which remains anchored to the membrane, a destabilizing effect implies the re-initiation of the proteolytic process (E-S formation). The situation is fundamentally different in the case of Aβ$_n$ substrates as they are no longer anchored in the membrane and their release and dilution into the extracellular milieu makes re-association with the enzyme unlikely. In support of our model, others have shown that PSEN pathogenic substitutions increase the dissociation rate of the γ-secretase-Aβ$_{42}$ complex (Okochi et al., 2013).

It is highly relevant that both APP and PSEN mutants promote the release of relatively long Aβ peptides (Aβ$_{43}$). Thus, while increments in toxic Aβ$_{42}$ are proposed as drivers of FAD (Potter et al., 2013), our findings raise the possibility that even longer Aβ species may have high pathogenic relevance. The neurotoxicity and high propensity for aggregation of Aβ$_{43}$ as well as its abundancy in AD brain tissue has been highlighted in previous studies (Saito et al., 2011; Welander et al., 2009). Thus, analysis of full Aβ profiles will become necessary when evaluating the effect of clinical mutations in APP and PSEN or other genes.

Figure 5:
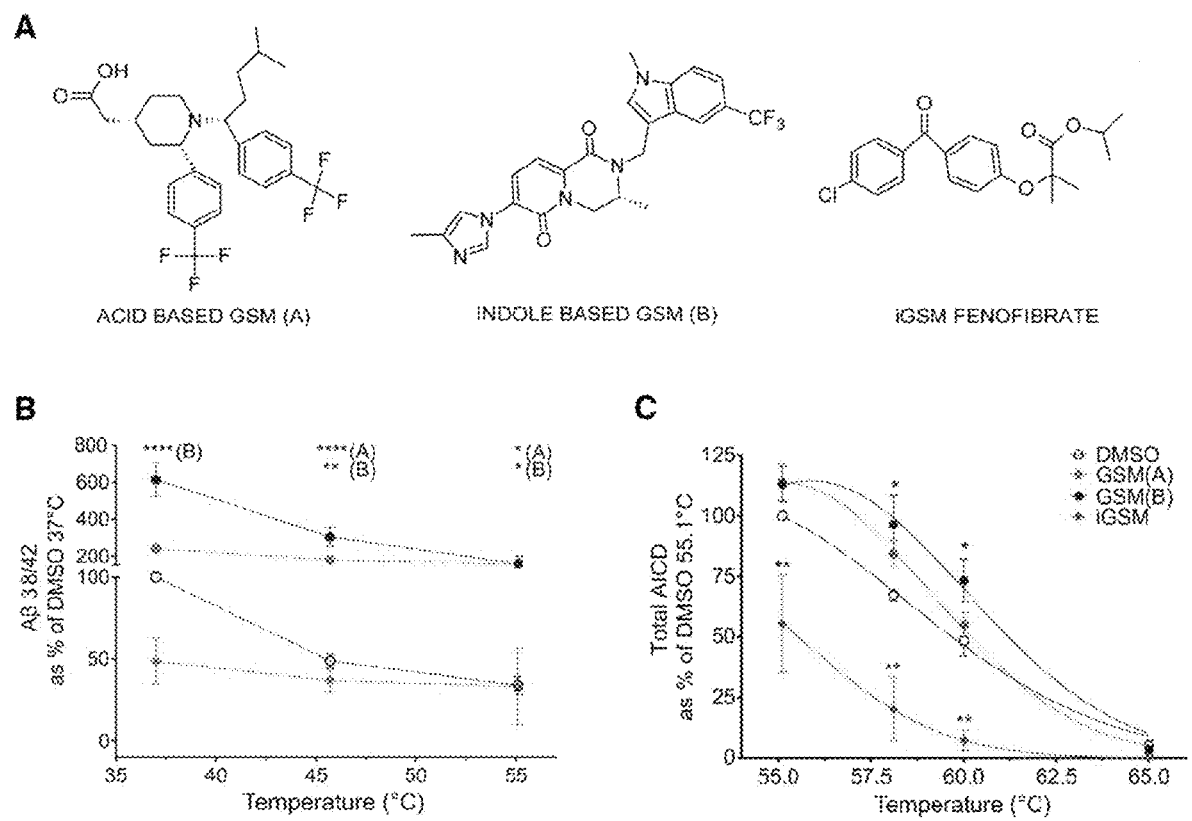
FIG. 5. Evaluation of modulators in γ-secretase thermo-activity assays

The novel concepts generated in these studies help to understand the mechanism of action of the candidate for AD therapeutics targeting γ-secretase, i.e. the GSMs (FIG. 5). The same holds true when explaining the inverse correlation between generation of Aβ$_{42/43}$ peptides and membrane thickness (Holmes et al., 2012; Winkler et al., 2012) and the high sensitivity of γ-secretase function to lipid environment changes (Holmes et al., 2012; Osenkowski et al., 2008). Besides providing fundamental novel mechanistic insights into the working of γ-secretase, the current application raises some additional interesting pathophysiological considerations. The significant changes in γ-secretase processivity observed upon mild temperature increment in vitro and in vivo suggest that fever could promote generation of amyloidogenic Aβ peptides. While further work is needed to investigate the relationship between fever and the occurrence of AD, it is interesting to notice that carriers of the M694V pyrin mutation associated with Familial Mediterranean Fever have been found to have a 3-fold higher risk for sporadic early-onset AD than those who were homozygous for the normal allele in an Italian population (Arra et al., 2006). In this study, sporadic AD patients carrying the M694V pyrin variant developed symptoms of AD 7 years earlier than the control SAD cohort and the effect was independent of the presence of the APOE4 allele. Whether this is caused by the occurrence of fever or other (unknown) effects of the mutation remains to be investigated. However, the fact that artificially induced fever in mice alters Aβ profiles provides experimental support to the idea.

Materials and Methods

Antibodies and Reagents

Antibodies were purchased as follows: anti-FLAG M2 from Sigma, Alexa 790 Goat anti-Mouse IgG from Invitrogen, 82E1 against human Aβ (N-term) from IBL, biotinylated anti-mouse IgG from Vector Laboratories and streptavidin-HRP from GE Healthcare. ELISA antibodies and γ-secretase modulators were obtained through collaboration with Janssen Pharmaceutica NV, Beerse, Belgium: JRF AB038 for Aβ1-38, JRF/cAb40/28 for Aβ1-40, JRF/cAb42/26 for Aβ1-42 and detection antibody JRF/AbN/25 against the N-terminus of Aβ. Elisa kit against amyloid β (1-43) (FL) was purchased from IBL. Fenofibrate was purchased from Sigma Aldrich. Synthetic β-Amyloid 1-38, 1-40, 1-42, 1-46 were purchased from rPeptide, β-Amyloid 1-43 from IBL and 1-45 from Anaspec. γ-Secretase inhibitor X purchased from Calbiochem. All reagents for MALDI-Mass Spectrometry used in this study were of HLPC grade. Acetonitrile (ACN) and trifluoroacetic acid (TFA), were purchased from Merck (Darmstadt, GER). Milli-Q water (ddH$_2$O; Millipore) was prepared in-house. Sinapinic acid (SA; Cat. No. 201345) and MALDI-MS protein calibration standard I (Cat. No. 206355) were purchased from Bruker Daltonics (Bremen, Germany).

Expression and Purification of Wild Type and Mutant C99-3xFLAG and Notch-3xFLAG Substrates Human wild type and mutant (T43I (T714I), I45F (I716F), V46F (V717F) and V46I(V717I)) APP$_{C99}$-3xFLAG and Notch-based (Notch-3xFLAG) substrates were expressed in COS1 or HEK cells and purified as previously described (Chavez-Gutierrez et al., 2008). Purity was assessed by SDS-PAGE and Coomassie staining (InstantBlue Protein Stain, Expedeon).

Expression and Purification of γ-Secretase Complexes

Human wild type or mutant (P88L, Y115H, M139V, L166P, R2781, E280A, G384A, L435F) PSEN1, NCT-GFP, APH1AL and PEN2 cDNAs were cloned into the pAcAB4 transfer vector (BD Biosciences). Co-transfection of the transfer vector (containing the heterologous genes) and flashBacGold™ DNA (Oxford Expression Technologies) in Sf9 cells allowed homologous recombination and production of baculoviruses bearing the four essential subunits of the γ-secretase complex. Protease complexes were expressed in Hi5 insect cells and purified as described in (Acx et al., 2014). Briefly, infected Hi5 cells were collected at 72 h post infection and lysed in 2% CHAPSO buffer (25 mM Pipes pH 7.4, 300 mM NaCl, 5% Glycerol, PI). Affinity purification was carried out using a high affinity anti-GFP nanobody covalently coupled to agarose beads (NHS-activated beads, GE Healthcare) in a 3:1 ratio (mg:mL). PreScission protease cleavage between NCT and GFP eluted untagged γ-secretase complexes (buffer composition: 25 mM Pipes pH 7.4, 150 mM NaCl, 0.5% CHAPSO, 5% Glycerol). Finally, removal of the GST-tagged PreScission protease by immunoaffinity pulldown using Glutathione Sepharose 4B (GE Healthcare) was performed and the purity of γ-secretase complexes was assessed by SDS-PAGE and Coomassie staining (InstantBlue Protein Stain, Expedeon).

Subjects

Human cortical specimens were obtained throughout collaboration with Queen Square Brain Bank for Neurological Disorders at University College London. All of the samples came from brains that were removed and placed in −80° C. within 65 hours postmortem. Samples were collected following protocols approved by respective ethical boards and written legal consents for the use of organs for medical research are available for each patient. All human protocols were approved by Medical Ethics Committee UZ KU Leuven, Belgium.

Detergent Resistant Membrane Preparation from Insect Cells and Human Brain Samples CHAPSO detergent resistant membranes (DRMs) were prepared from human brain frontal cortices after careful removal of leptomeninges and blood vessels, as previously described (Kakuda et al., 2012; Szaruga et al., 2015). Around 200 mg blocks of tissue were homogenized in ~10 volumes of 10% sucrose in MBS buffer (25 mM MES, pH 6.5, 150 mM NaCl) containing 1% CHAPSO (Sigma) and protease inhibitors (Complete, Roche). DRMs from insect cells were prepared from Hi5 cells overexpressing PSEN1/APH1A γ-secretase complexes (WT or mutant complexes containing PSEN1 pathogenic mutations P88L, Y115H, M139V, L166P, R278I, E280A, G384A or L435F). Total membranes were prepared from 200 ml Hi5 cell cultures and membrane pellets were homogenized in ~2.5 ml of 10% sucrose in MBS buffer containing 1% CHAPSO (Sigma) and protease inhibitors. Brain or cell membrane homogenates were mixed with equal volume of 70% sucrose in MBS buffer, 4 ml was placed at the bottom of an ultracentrifuge tube (Beckman, 344059) and successively overlaid with 4 ml of 35% sucrose (MBS) and 4 ml of 5% sucrose (MBS). Samples were centrifuged at 39,000 rpm for 20 h at 4° C. on a SW 41 Ti rotor (Beckman). After centrifugation the DRM fraction (interface of 5%/35% sucrose) was carefully collected, rinsed in 20 mM PIPES, pH 7, 250 mM sucrose, 1M EGTA and recentrifuged twice (100,000 g, 60 min, 4° C.). The resultant pellet was resuspended with above buffer and stored at −80° C. until use.

Evaluation of γ-secretase Activity in Cell Culture

To assess the effect of elevated temperature on Aβ production, HEK293 cells stably expressing human $APP_{695}$ KM670/671 NL (Swedish) were plated at $1\times10^6$ cells/9 cm² well; after 24 h, cells were washed with serum-free media and medium refreshed (1 ml). Cells were immediately placed at 37 or 42° C. and after 1 h incubation the extracellular media was collected for Aβ ELISA analyses and cell viability assessed (trypan blue staining). To determine the effects of mutations in APP on Aβ production, wild type HEK 293 cells were transfected with pSG5-based expression vectors bearing wild type or mutant $APP_{C99}$3xFLAG cDNAs. At 36 h post-transfection, cells were rinsed and medium refreshed. Extracellular media was collected after 4h incubation at 37° C. For all experiments, cells were cultured in Dulbecco's modified Eagle's medium/F-12 containing 10% fetal bovine serum and sAβ were analysed by MSD ELISA.

γ-Secretase In Vitro Thermo-Activity Assays

Proteolytic reactions were performed using purified ~10 nM PSEN1/APH1A γ-secretase complexes (Acx et al., 2014) and saturating concentrations of purified recombinant FLAG tagged substrates in 0.25% CHAPSO, 2.5% DMSO (or 10 µM GSM, 100 µM Fenofibrate), 0.1% Phosphatidylcholine, 150 mM NaCl and 25 mM PIPES over a temperature gradient ranging from 37° C.-65° C. for 20 min (except for the severe P88L mutant protease which activity was measured after 1 h incubation and with 10× more enzyme). Enzyme mixes (containing all components excepting substrate) and substrate dilutions were pre-incubated separately at the indicated temperature for 10 min. After pre-incubation, substrate was added to the enzyme mix and proteolysis proceeded for 20 min or 1 h for the P88L-PSEN mutant. Final substrate concentrations in assays were 1.75 µM C99-3xFLAG or 2 µM Notch-3xFLAG unless otherwise indicated.

γ-Secretase thermo-activity assays using $A\beta_{45}$ or $A\beta_{46}$ synthetic peptides as substrates and purified wild type γ-secretase were carried out as indicated above with the following modifications: synthetic Aβ peptides were diluted in DMSO and proteolytic reactions were incubated for 1 hour at the indicated temperatures.

Thermo-activity analyses using DRMs as source of enzyme were performed similarly, but reactions contained 0.6 µg/µl or 1 µg/µl protein for DRMs prepared from Hi5 insect cells overexpressing γ-secretase components or human brain samples, respectively. Assays were carried out for 20 min for DRMs derived from insect cells or 4 h for DRMs prepared from human brain samples in saline MBS buffer (150 mM NaCl, 25 mM MES), 0.1% DMSO, 1 nnM EGTA and protease inhibitors (Complete, ROCHE) with purified substrates at saturating concentrations. Temperature gradients ranging from 37° C.-60° C. and 60°-80° C. were set for DRM analyses. All thermo-activity assays were performed on a PCR thermocycler (Biorad T100).

Quantification of γ-Secretase Endopeptidase Activity

γ-Secretase endopeptidase products (ICD-3XFLAG) generated in the proteolytic assays were quantified by SDS-PAGE western immunoblot and/or MALDI-MS (see MALDI-MS analysis). In the first case, reactions were mixed with one volume of methanol-chloroform (1:2, v/v) to remove hydrophobic molecules (lipids, substrate and membrane proteins) and aqueous fractions containing ICD products were analyzed by SDS-PAGE western immunoblot using anti-FLAG M2 antibody and quantified with Odyssey infrared imaging system.

Quantification of Aβ Production by ELISA $A\beta_{38}$, $A\beta_{40}$ and $A\beta_{42}$ product levels were quantified on Multi-Spot 96 well plates pre-coated with anti-$A\beta_{38}$, $A\beta_{40}$, and Aβ42 antibodies obtained from Janssen Pharmaceutica using multiplex MSD technology. MSD plates were blocked with 150 µl/well 0.1% casein buffer for 1.5 h at room temperature (600 rpm) and rinsed 5× with 200 µl/well washing buffer (PBS+0.05% Tween-20). Twenty five µl of SULFO-TAG JRF/AbN/25 detection antibody diluted in blocking buffer was mixed with 25 µl of standards (synthetic human Aβ1-38, Aβ1-40, Aβ1-42 peptides) or reaction samples diluted in blocking buffer and 50 µl loaded per well. For the quantification of Aβ peptides generated in activity assays using synthetic Aβ45 and Aβ46 as substrates, reactions with no enzyme were loaded to determine background levels. After overnight incubation at 4° C., plates were rinsed with washing buffer and 150 µl/well of the 2× MSD Read Buffer T (tris-based buffer containing tripropylamine, purchased from Meso Scale Discovery) was added. Plates were immediately read on MSD Sector Imager 6000. Aβ43 product levels were quantified with β-Amyloid 1-43 kit from IBL according to manufacturer's instructions. Aβ38, Aβ40 and Aβ42 product levels in proteolytic reactions using DRMs were analyzed by MALDI-MS.

Detection of Aβ Product Profiles in Urea Gels

Aβ-products were analyzed in urea-based SDS-PAGE (Wiltfang et al., 2002) (11% T/5% C polyacrylamide and 0.4M $H_2SO_4$ in the separation gel pH=8.1) followed by western immunoblot with 82E1 antibody, biotinylated anti-mouse IgG and streptavidin-HRP. Signals were detected using ECL chemiluminescence with Fujifilm LAS-3000 Imager.

MALDI-MS Sample Preparation and Analysis of γ-Secretase Products

Sample preparation for MALDI-TOF MS in vitro Aβ/AICD profiling was performed as follows: A total volume of 15 µl of in vitro γ-secretase activity reactions were mixed with 15 µl SA (38 mg/mL in water/ACN/TFA 40/60/0.2 (v/v/v)) (Munteanu et al., 2012) without any additional purification or enrichment steps. Thereafter, 1 µl (8 technical replicates) of the matrix-analyte mix was applied on top of the thin SA layer using the dried droplet preparation (double layer) and air dried (Munteanu and Hopf, 2016). All mass spectra were acquired on an UltrafleXtreme MALDI-TOF/TOF mass spectrometer (Bruker Daltonics) equipped with a 2 kHz Smartbeam™ laser using the AutoXecute function of the FlexControl 3.4 acquisition software: Briefly, each spectrum was acquired in linear positive mode within the mass range of m/z 2,500 to 20,000 with a low mass gate at m/z 2,000. 5,000 laser shots were automatically accumulated for each sample by random walk. Mass spectrometer parameters (Munteanu and Hopf, 2016) were balanced for optimal resolution and sensitivity in the Aβ peptide mass range (4-5 kDa). Subsequently, protein mass spectra were baseline-subtracted and externally calibrated in Flex Analysis 3.4 (Bruker Daltonics) using the protein calibration standard I (Bruker Daltonics). Average MALDI MS profiles were generated from eight single spectra using ClinProTools 3.0 software (Bruker Daltonics) (CPT). The following modified CPT processing parameters ((Munteanu and Hopf, 2016)) were used: Resolution 1000: Convex Hull baseline subtraction with a baseline flatness value of 0.75: Mass Range (m/z) 2,500-20,000: Spectra were recalibrated, allowing a mass tolerance of 500 ppm matched on 30% of the peaks. Not recalibrated spectra were excluded. Peak picking was performed on total average spectra (based on intensity calculation and zero level integration type) using an intensity signal to noise (S/N) threshold >5.

High Resolution MALDI FT-ICR

Monoisotopically resolved protein signals were recorded using a 7T Solarix XR MALDI FT-ICR mass spectrometer equipped with an Apollo II dual MALDI/ESI ion source and a 2 kHz Smartbeam II laser (Bruker Daltonics). Sample preparation for MALDI-FT-ICR measurements was done as previously described. Data were acquired in positive ion mode from 150 to 10,000 m/z using magnitude mode and 4M data size with a resolving power of 390,000 at m/z 400 and ~40,000 at m/z 4,000, respectively, and a free induction decay of 2.9 s. The following tuning parameters were used; Ion transfer (Funnel 1 100 V; Skimmer 1 45 V; Funnel RF Amplitude 150 Vpp; Octopole 2 MHz, RF Amplitude 350 Vpp; RF Frequency 1.4 MHz, 1200 Vpp; Transfer Optics Time of Flight 2.9 ms, Frequency 1 MHz, FR Amplitude 350 Vpp; Q1 Mass 4,000 m/z. Excitation Mode (Sweep Excitation; Sweep Step Time 15 ps), Ramped Power Excitation (Continuous, 14-28%). A total accumulation of 100 scans was done. Before measurement the MALDI-FT-ICR MS was externally calibrated using the Bruker protein calibration mix I containing the following components (Ubiquitin $[M+H]^+$ m/z 8560.623989, Insulin $[M+H]^+$ m/z 5730.608146 and the signal corresponding to the doubly charged Ubiquitin $[M+2H]^{2+}$ m/z 4280.815633). Spectra recalibration was done by performing a one-point internal recalibration on the most prominent amyloid beta signal in the analysis and was done using the software Data Analysis 4.4 (Bruker Daltonics). Computational analysis and mass matching were performed using the Bruker Biotools 3.2 SR5 (Bruker Daltonics) software.

Elevation of Body Temperature in Mice

Eleven to sixteen-week-old female APP NL mice were injected intraperitoneally with 30 µg of LPS (Sigma-Aldrich) in 500 µl of sterile saline. Age-matched controls were treated simultaneously with saline only. Mice injected with LPS were immediately placed in cages preheated with a heating pad, a red light lamp and a 60 W bulb to ~38.5° C. Mice core body temperature raised within 25 min to 40° C. (±0.5° C.) and then maintainated at 39.9° C. (±0.6° C.) for 100 min (Figure S5). Mice rectal temperature was monitored every 25 min (see FIG. 11). Control mice were kept at room temperature (RT, 22-24° C.) and subjected to the same handling. At the end of the experiment mice were sacrificed in CO2 and decapitated. Collected blood was used to isolate plasma by 10 min centrifugation at 1500 g. Aβ38, Aβ40, and Aβ42 steady-state levels in plasma were analyzed by ELISA (multiplex MSD technology). The protocol was approved by ethical committee of KU Leuven (project number: 142/2015).

Statistical Analysis

All statistical analysis was performed using GraphPad Prism software. Statistical evaluation of MALDI-MS data of drug/temperature effects on γ-secretase Aβ/AICD activity, were done on total ion count normalized (CPT) average mass spectra. Briefly, eight single mass spectra were processed as described above, and average intensity values (arbitrary units) were extracted for defined Aβ peptides or AICDs within a mass tolerance window of 500 ppm and transferred to GraphPad Prism software for further analysis and visualization. Linear MALDI TOF MS signals corresponding to amyloid beta were confirmed by high resolution MALDI-FT-ICR analysis with a mass accuracy <<5 ppm.

REFERENCES

Acx, H., Chávez-Gutiérrez, L., Serneels, L., Lismont, S., Benurwar, M., Elad, N., De Strooper, B., Chavez-Gutierrez, L., Serneels, L., Lismont, S., et al. (2014). Signature amyloid beta profiles are produced by different gamma-secretase complexes. J. Biol. Chem. 289, 4346-4355.

Arra, M., Emanuele, E., Martinelli, V., Minoretti, P., Bertona, M., and Geroldi, D. (2006). The M694V variant of the familial Mediterranean fever gene is associated with sporadic early-onset Alzheimer's disease in an Italian population sample. Dement. Geriatr. Cogn. Disord. 23, 55-59.

Bai, X., Yan, C., Yang, G., Lu, P., Sun, L., Zhou, R., Scheres, S. H. W., and Shi, Y. (2015a). An atomic structure of human γ-secretase. Nature.

Bai, X. C., Rajendra, E., Yang, G., Shi, Y., and Scheres, S. H. (2015b). Sampling the conformational space of the catalytic subunit of human gamma-secretase. Elife 4.

Baker, R. P., and Urban, S. (2012). Architectural and thermodynamic principles underlying intramembrane protease function. Nat. Chem. Biol. 8, 759-768.

Barrett, P. J., Song, Y., Van Horn, W. D., Hustedt, E. J., Schafer, J. M., Hadziselimovic, A., Beel, A. J., and Sanders, C. R. (2012). The Amyloid Precursor Protein Has a Flexible Transmembrane Domain and Binds Cholesterol. Science (80-). 336, 1168-1171.

Belyaev, a S., and Roy, P. (1993). Development of baculovirus triple and quadruple expression vectors: co-expression of three or four bluetongue virus proteins and the synthesis of bluetongue virus-like particles in insect cells. Nucleic Acids Res. 21, 1219-1223.

Bolduc, D. M., Montagna, D. R., Seghers, M. C., Wolfe, M. S., and Selkoe, D. J. (2016). The amyloid-beta forming tripeptide cleavage mechanism of γ-secretase. Elife 5, 1-4.

Chavez-Gutierrez, L., Tolia, A., Maes, E., Li, T., Wong, P. C., de Strooper, B., Chávez-Gutiérrez, L., Tolia, A., Maes, E., Li, T., et al. (2008). Glu(332) in the Nicastrin ectodomain is essential for gamma-secretase complex maturation but not for its activity. J Biol Chem 283, 20096-20105.

Chávez-Gutiérrez, L., Bammens, L., Benilova, I., Vandersteen, A., Benurwar, M., Borgers, M., Lismont, S., Zhou, L., Van Cleynenbreugel, S., Esselmann, H., et al. (2012). The mechanism of γ-Secretase dysfunction in familial Alzheimer disease. EMBO J. 31, 2261-2274.

Dickey, S. W., Baker, R. P., Cho, S., and Urban, S. (2013). Proteolysis inside the membrane is a rate-governed reaction not driven by substrate affinity. Cell 155, 1270-1281.

Dimitrov, M., Alattia, J.-R., Lemmin, T., Lehal, R., Fligier, A., Houacine, J., Hussain, I., Radtke, F., Dal Peraro, M., Beher, D., et al. (2013). Supplementary—Alzheimer's disease mutations in APP but not γ-secretase modulators affect epsilon-cleavage-dependent AICD production. Nat. Commun. 4, 2246.

Elad, N., De Strooper, B., Lismont, S., Hagen, W., Veugelen, S., Arimon, M., Horre, K., Berezovska, O., Sachse, C., and Chavez-Gutierrez, L. (2014). The dynamic conformational landscape of γ-secretase. J. Cell Sci. 128, 589-598.

Fernandez, M. A., Klutkowski, J. A., Freret, T., and Wolfe, M. S. (2014). Alzheimer presenilin-1 mutations dramatically reduce trimming of long amyloid β-peptides (Aβ) by γ-secretase to increase 42-to-40-residue Aβ. J. Biol. Chem. 289, 31043-31052.

Funamoto, S., Sasaki, T., Ishihara, S., Nobuhara, M., Nakano, M., Watanabe-Takahashi, M., Saito, T., Kakuda, N., Miyasaka, T., Nishikawa, K., et al. (2013). Substrate ectodomain is critical for substrate preference and inhibition of γ-secretase. Nat. Commun. 4, 2529.

Goate, A., Chartier-Harlin, M. C., Mullan, M., Brown, J., Crawford, F., Fidani, L., Giuffra, L., Haynes, A., Irving, N., and James, L. (1991). Segregation of a missense mutation in the amyloid precursor protein gene with familial Alzheimer's disease. Nature 349, 704-706.

Holmes, O., Paturi, S., Ye, W., Wolfe, M. S., and Selkoe, D. J. (2012). Effects of membrane lipids on the activity and processivity of purified γ-secretase. Biochemistry 51, 3565-3575.

Jiang, Q., Detolla, L., Singh, I. S., Gatdula, L., Fitzgerald, B., van Rooijen, N., Cross, A. S., and Hasday, J. D. (1999). Exposure to febrile temperature upregulates expression of pyrogenic cytokines in endotoxin-challenged mice. Am J Physiol 276, R1653-60.

Jung, J. I., Price, A. R., Ladd, T. B., Ran, Y., Park, H.-J., Ceballos-Diaz, C., Smithson, L. a., Hochhaus, G., Tang, Y., Akula, R., et al. (2015). Cholestenoic acid, an endogenous cholesterol metabolite, is a potent γ-secretase modulator. Mol. Neurodegener. 10, 29.

Kakuda, N., Shoji, M., Arai, H., Furukawa, K., Ikeuchi, T., Akazawa, K., Takami, M., Hatsuta, H., Murayama, S., Hashimoto, Y., et al. (2012). Altered γ-secretase activity in mild cognitive impairment and Alzheimer's disease. EMBO Mol. Med. 4, 344-352.

Kornilova, A. Y., Bihel, F., Das, C., and Wolfe, M. S. (2005). The initial substrate-binding site of γ-secretase is located on presenilin near the active site. PNAS 102: 3230-3235.

Kukar, T., Murphy, M. P., Eriksen, J. L., Sagi, S. a., Weggen, S., Smith, T. E., Ladd, T., Khan, M. a., Kache, R., Beard, J., et al. (2005). Diverse compounds mimic Alzheimer disease-causing mutations by augmenting Aβ42 production. Nat. Med. 11, 545-550.

Li, Y., Lu, S. H., Tsai, C. J., Bohm, C., Qamar, S., Dodd, R. B., Meadows, W., Jeon, A., McLeod, A., Chen, F., et al. (2014). Structural interactions between inhibitor and substrate docking sites give insight into mechanisms of human PS1 complexes. Structure 22, 125-135.

Lleo, A., Berezovska, O., Herl, L., Raju, S., Deng, A., Bacskai, B. J., Frosch, M. P., Irizarry, M., and Hyman, B. T. (2004). Nonsteroidal anti-inflammatory drugs lower Abeta42 and change presenilin 1 conformation. Nat. Med. 10, 1065-1066.

Matsumura, N., Takami, M., Okochi, M., Wada-Kakuda, S., Fujiwara, H., Tagami, S., Funamoto, S., Ihara, Y., and Morishima-Kawashima, M. (2014). γ-secretase associated with lipid rafts: Multiple interactive pathways in the stepwise processing of β-carboxylternninal fragment. J. Biol. Chem. 289, 5109-5121.

Moin, S. M., and Urban, S. (2012). Membrane immersion allows rhomboid proteases to achieve specificity by reading transmembrane segment dynamics. Elife 2012.

Munteanu, B., Von Reitzenstein, C., Hansch, G. M., Meyer, B., and Hopf, C. (2012). Sensitive, robust and automated protein analysis of cell differentiation and of primary human blood cells by intact cell MALDI mass spectrometry biotyping. Anal. Bioanal. Chem. 404, 2277-2286.

Munteanu B. and C. Hopf (2016). Whole/Intact Cell MALDI MS Biotyping in Mammalian Cell Analysis. In Advances in MALDI and Laser-Induced Soft Ionization Mass Spectrometry, Springer International Publishing: Cham., R. Cramer, ed. pp. 249-262.

Ohki, Y., Shimada, N., Tominaga, A., Osawa, S., Higo, T., Yokoshima, S., Fukuyama, T., Tomita, T., and Iwatsubo, T. (2014). Binding of longer Aβ to transmembrane domain 1 of presenilin 1 impacts on Aβ42 generation. Mol. Neurodegener. 9, 7.

Okochi, M., Fukumori, A., Jiang, J., Itoh, N., Kimura, R., Steiner, H., Haass, C., Tagami, S., and Takeda, M. (2006). Secretion of the Notch-1 Abeta-like peptide during Notch signaling. J. Biol. Chem. 281, 7890-7898.

Okochi, M., Tagami, S., Yanagida, K., Takami, M., Kodama, T. S., Mori, K., Nakayama, T., Ihara, Y., and Takeda, M. (2013). γ-secretase modulators and presenilin 1 mutants act differently on presenilin/γ-secretase function to cleave Aβ42 and Aβ43. Cell Rep. 3, 42-51.

Osenkowski, P., Ye, W., Wang, R., Wolfe, M. S., and Selkoe, D. J. (2008). Direct and potent regulation of gamma-secretase by its lipid microenvironment. J Biol Chem 283, 22529-22540.

Potter, R., Patterson, B. W., Elbert, D. L., Ovod, V., Kasten, T., Sigurdson, W., Mawuenyega, K., Blazey, T., Goate, A., Chott, R., et al. (2013). Increased in Vivo Amyloid- 42 Production, Exchange, and Loss in Presenilin Mutation Carriers. Sci. Transl. Med. 5, 189ra77.

Saito, T., Suemoto, T., Brouwers, N., Sleegers, K., Funamoto, S., Mihira, N., Matsuba, Y., Yamada, K., Nilsson, P., Takano, J., et al. (2011). Potent amyloidogenicity and pathogenicity of Aβ43. Nat. Neurosci. 14, 1023-1032.

Saito, T., Matsuba, Y., Mihira, N., Takano, J., Nilsson, P., Itohara, S., Iwata, N., and Saido, T. C. (2014). Single App knock-in mouse models of Alzheimer's disease. Nat. Neurosci. 17, 661-663.

Sato, T., Dohmae, N., Qi, Y., Kakuda, N., Misonou, H., Mitsumori, R., Maruyama, H., Koo, E. H., Haass, C., Takio, K., et al. (2003). Potential link between amyloid beta-protein 42 and C-terminal fragment gamma 49-99 of beta-amyloid precursor protein. J. Biol. Chem. 278, 24294-24301.

Sherrington, R., Rogaev, E. I., Liang, Y., Rogaeva, E. A., Levesque, G., Ikeda, M., Chi, H., Lin, C., Li, G., Holman, K., et al. (1995). Cloning of a gene bearing missense mutations in early-onset familial Alzheimer's disease. Nature 375, 754-760.

De Strooper, B., and Chávez Gutiérrez, L. (2015). Learning by failing: ideas and concepts to tackle γ-secretases in Alzheimer's disease and beyond. Annu. Rev. Pharmacol. Toxicol. 55, 419-437.

De Strooper, B., Saftig, P., Craessaerts, K., Vanderstichele, H., Guhde, G., Annaert, W., Von Figura, K., and Van Leuven, F. (1998). Deficiency of presenilin-1 inhibits the normal cleavage of amyloid precursor protein. Nature 391, 387-390.

De Strooper, B., Annaert, W., Cupers, P., Saftig, P., Craessaerts, K., Mumm, J. S., Schroeter, E. H., Schrijvers, V., Wolfe, M. S., Ray, W. J., et al. (1999). A presenilin-1-dependent gamma-secretase-like protease mediates release of Notch intracellular domain. Nature 398, 518-522.

Svedruzic, Z. M., Popovic, K., Smoljan, I., and Sendula-Jengic, V. (2012). Modulation of gamma-secretase activity by multiple enzyme-substrate interactions: implications in pathogenesis of Alzheimer's disease. PLoS One 7, e32293.

Szaruga, M., Veugelen, S., Benurwar, M., Lismont, S., Sepulveda-Falla, D., Lleo, A., Ryan, N. S., Lashley, T., Fox, N. C., Murayama, S., et al. (2015). Qualitative changes in human γ-secretase underlie familial Alzheimer's disease. J. Exp. Med. 212, 2003-2013.

Takami, M., Nagashima, Y., Sano, Y., Ishihara, S., Morishima-Kawashima, M., Funamoto, S., and Ihara, Y. (2009). gamma-Secretase: successive tripeptide and tetrapeptide release from the transmembrane domain of beta-carboxyl terminal fragment. J. Neurosci. 29, 13042-13052.

Takeo, K., Tanimura, S., Shinoda, T., Osawa, S., Zahariev, I. K., Takegami, N., Ishizuka-Katsura, Y., Shinya, N., Takagi-Niidome, S., Tominaga, A., et al. (2014). Allosteric regulation of γ-secretase activity by a phenylimidazole-type γ-secretase modulator. Proc. Natl. Acad. Sci. U.S.A. 111, 10544-10549.

Uemura, K., Lill, C. M., Li, X., Peters, J. A., Ivanov, A., Fan, Z., DeStrooper, B., Bacskai, B. J., Hyman, B. T., and Berezovska, O. (2009). Allosteric modulation of PS1/gannnna-secretase conformation correlates with amyloid beta(42/40) ratio. PLoS One 4, e7893.

Uemura, K., Farner, K. C., Hashimoto, T., Nasser-Ghodsi, N., Wolfe, M. S., Koo, E. H., Hyman, B. T., and Berezovska, O. (2010). Substrate docking to gamma-secretase allows access of gamma-secretase modulators to an allosteric site. Nat. Commun. 1, 130.

Veugelen, S., Saito, T., Saido, T. C., Chávez-Gutiérrez, L., and De Strooper, B. (2016). Familial Alzheimer's Disease Mutations in Presenilin Generate Amyloidogenic Aβ Peptide Seeds. Neuron 90, 410-416.

Wahlster, L., Arimon, M., Nasser-Ghodsi, N., Post, K. L., Serrano-Pozo, A., Uemura, K., and Berezovska, O. (2013). Presenilin-1 adopts pathogenic conformation in normal aging and in sporadic Alzheimer's disease. Acta Neuropathol. 125, 187-199.

Wahrle, S., Das, P., Nyborg, A. C., McLendon, C., Shoji, M., Kawarabayashi, T., Younkin, L. H., Younkin, S. G., and Golde, T. E. (2002). Cholesterol-dependent gamma-secretase activity in buoyant cholesterol-rich membrane microdomains. Neurobiol. Dis. 9, 11-23.

Weggen, S., Eriksen, J. L., Das, P., Sagi, S. a, Wang, R., Pietrzik, C. U., Findlay, K. a, Smith, T. E., Murphy, M. P., Bulter, T., et al. (2001). A subset of NSAIDs lower amyloidogenic Abeta42 independently of cyclooxygenase activity. Nature 414, 212-216.

Welander, H., Franberg, J., Graff, C., SundstrOnn, E., Winblad, B., and Tjernberg, L. O. (2009). Aβ43 is more frequent than Aβ40 in amyloid plaque cores from Alzheimer disease brains. J. Neurochem. 110, 697-706.

Wiltfang, J., Esselmann, H., Bibl, M., Smirnov, a., Otto, M., Paul, S., Schmidt, B., Klafki, H. W., Maier, M., Dyrks, T., et al. (2002). Highly conserved and disease-specific patterns of carboxyternninally truncated Aβ peptides 1-37/38/39 in addition to 1-40/42 in Alzheimer's disease and in patients with chronic neuroinflammation. J. Neurochem. 81, 481-496.

Winkler, E., Kamp, F., Scheuring, J., Ebke, A., Fukumori, A., and Steiner, H. (2012). Generation of Alzheimer disease-associated amyloid Aβ42/43 peptide by γ-secretase can be inhibited directly by modulation of membrane thickness. J. Biol. Chem. 287, 21326-21334.

Wolfe, M. S., Xia, W., Ostaszewski, B. L., Diehl, T. S., Kimberly, W. T., and Selkoe, D. J. (1999). Two transmembrane aspartates in presenilin-1 required for presenilin endoproteolysis and gamma-secretase activity. Nature 398, 513-517.

The invention claimed is:

1. An in vitro method for testing a compound, the method comprising:
   determining a first temperature that thermally destabilizes a gamma-secretase complex by measuring a decrease in the ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ peptides in a first system at the first temperature as compared to the ratio of $A\beta_{38}/A\beta_{42}$ or of $A\beta_{40}/A\beta_{43}$ or of $A\beta_{40}/A\beta_{42}$ or of $(A\beta_{38}+A\beta_{40})/(A\beta_{42}+A\beta_{43})$ at a second temperature under identical conditions except the second temperature being lower than the first temperature;
   the first system comprising:
      the gamma-secretase complex, and
      a polypeptide comprising an amino acid sequence with at least 95% amino acid identity to the full length of SEQ ID NO: 4,
   administering a test compound to an in vitro second system, the second system comprising:
   the gamma-secretase complex, and
   a polypeptide comprising of an amino acid sequence with at least 95% amino acid identity to the full length of SEQ ID NO: 4, and
   measuring the amounts of $A\beta_{38}$, $A\beta_{40}$, $A\beta_{42}$, and $A\beta_{43}$ peptides in the second system as compared to an otherwise identical control system under identical conditions except for the presence of the test compound.

2. The method according to claim 1, wherein the in vitro second system is a cell free system, and wherein the first temperature is a temperature from about 35° C. to about 65° C.

3. The method according to claim 2, wherein the first temperature is from about 37° C. to about 55° C.

4. The method according to claim 2, wherein the second system comprises a detergent resistant membrane preparation.

5. The method according to claim 1, wherein the second system is a cell-based system, and wherein the first temperature is a temperature of 37° C. to 42° C.

6. The method according to claim 1, wherein the first system and the second system comprise the gamma-secretase complex and a wherein the amino acid sequence has at least 95% amino acid identity to the full length of SEQ ID NO: 1.

7. The method according to claim 1, wherein the amino acid sequence has at least 95% identity to the full length of SEQ ID NO: 2.

8. The method according to claim 1, wherein the amino acid sequence has at least 95% identity to the full length of SEQ ID NO: 3.

9. The method according to claim 1, wherein measuring the amount of $A\beta_{38}$, $A\beta_{40}$, $A\beta_{42}$, and $A\beta_{43}$ peptides in the second system comprises immune-based detection.

10. The method according to claim 1, wherein measuring the amount of $A\beta_{38}$, $A\beta_{40}$, $A\beta_{42}$, and $A\beta_{43}$ peptides in the second system comprises mass spectrometry.

11. The method according to claim 1, wherein measuring the amount of $A\beta_{38}$, $A\beta_{40}$, $A\beta_{42}$, and $A\beta_{43}$ peptides in the second system comprises immune- and mass spectrometry-based detection.

* * * * *